(12) United States Patent
Liu et al.

(10) Patent No.: US 12,036,292 B2
(45) Date of Patent: Jul. 16, 2024

(54) HETEROBIARYL COMPOUNDS AND IMAGING AGENTS FOR IMAGING HUNTINGTIN PROTEIN

(71) Applicant: CHDI Foundation, Inc., New York, NY (US)

(72) Inventors: Longbin Liu, Thousand Oaks, CA (US); Celia Dominguez, Los Angeles, CA (US); Xuemei Chen, Voorheesville, NY (US); John E. Mangette, Town of Lancaster, NY (US)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 17/395,055

(22) Filed: Aug. 5, 2021

(65) Prior Publication Data

US 2022/0040336 A1 Feb. 10, 2022

Related U.S. Application Data

(60) Provisional application No. 63/062,310, filed on Aug. 6, 2020.

(51) Int. Cl.
| | | |
|---|---|---|
| *A61K 51/04* | (2006.01) | |
| *C07D 239/28* | (2006.01) | |
| *C07D 401/12* | (2006.01) | |
| *C07D 401/14* | (2006.01) | |
| *C07D 403/06* | (2006.01) | |
| *C07D 471/04* | (2006.01) | |

(52) U.S. Cl.
CPC ........ *A61K 51/0459* (2013.01); *C07D 239/28* (2013.01); *C07D 401/12* (2013.01); *C07D 401/14* (2013.01); *C07D 403/06* (2013.01); *C07D 471/04* (2013.01); *C07B 2200/05* (2013.01)

(58) Field of Classification Search
CPC .............. A61K 51/0459; C07D 239/28; C07D 401/12; C07D 401/14; C07D 403/06; C07D 471/04; C07B 2200/05

USPC ........................................................ 424/1.81
See application file for complete search history.

(56) References Cited

U.S. PATENT DOCUMENTS

| | | | |
|---|---|---|---|
| 8,536,186 | B2 | 9/2013 | Wityak et al. |
| 8,883,785 | B2 | 11/2014 | Dominguez et al. |
| 9,145,373 | B2 | 9/2015 | Wityak et al. |
| 9,260,422 | B2 | 2/2016 | Dominguez et al. |
| 9,428,464 | B2 | 8/2016 | Courtney et al. |
| 9,649,310 | B2 | 5/2017 | Dominguez et al. |
| 9,981,918 | B2 | 5/2018 | Toledo-Sherman et al. |
| 2010/0168084 | A1 | 7/2010 | Huber et al. |

FOREIGN PATENT DOCUMENTS

| | | | |
|---|---|---|---|
| WO | WO 03/004472 A1 | 1/2003 | |
| WO | WO 03/051851 A1 | 6/2003 | |
| WO | WO 2010/017179 A1 | 2/2010 | |
| WO | WO 2010/137351 A1 | 12/2010 | |
| WO | WO 2011/091153 A1 | 7/2011 | |
| WO | WO 2013/016488 A1 | 1/2013 | |
| WO | WO 2013/033068 A1 | 3/2013 | |
| WO | WO 2013/033085 A1 | 3/2013 | |
| WO | WO 2014/049488 A1 | 4/2014 | |
| WO | WO 2016/033445 A1 | 3/2016 | |
| WO | WO-2016033445 A1 * | 3/2016 | ........... A61K 51/041 |

OTHER PUBLICATIONS

International Search Report and Written Opinion dated Nov. 12, 2021 for PCT/US2021/044702, 13 pages.

* cited by examiner

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided herein are certain compounds and imaging agents useful for detecting a disease or condition associated with protein aggregation, compositions thereof, and methods of their use.

14 Claims, No Drawings

HETEROBIARYL COMPOUNDS AND IMAGING AGENTS FOR IMAGING HUNTINGTIN PROTEIN

CROSS REFERENCE TO RELATED APPLICATIONS

This application claims priority to U.S. Provisional Application No. 63/062,310, filed Aug. 6, 2020, which is incorporated herein by reference for all purposes.

FIELD

Provided herein are compounds and imaging agents useful for detecting, treating, or preventing a disease or condition associated with protein aggregation, compositions thereof, and methods of their use.

BACKGROUND

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The introduction of high-resolution molecular imaging technology is considered by many experts as a major breakthrough.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Molecular probes labeled with positron-emitting radionuclides and associated PET imaging assays are under development to target, detect, visualize, and quantify various extracellular and intracellular molecules and processes associated with various diseases.

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It is believed that polyglutamate domain expansion may induce conformational changes in the huntingtin (HTT) protein, which may lead to formation of aggregates. HD has a prevalence of 5-10 cases per 100,000 worldwide, which makes it the most common inherited neurodegenerative disorder.

Consistent with other medical conditions, treatments for HD are ideally initiated at or before early signs of disease. Thus, early indicators of disease are highly desirable.

In view of the central role of the accumulation of aggregated forms of proteins in the pathogenesis of neurodegenerative conditions including HD, there is a need for molecules that bind to such proteins with high sensitivity and specificity and that permit molecular imaging.

SUMMARY

The present disclosure relates to compounds useful for imaging huntingtin protein. Some embodiments provide for a compound of Formula I as described herein, wherein the compound is optionally labeled with one or more radioactive isotopes. In some embodiments, the compound of Formula I contains one or more positron-emitting radioactive isotopes selected from $^{11}C$, $^{13}N$, $^{15}O$, and $^{18}F$.

In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are imaging agents comprising a compound described herein, wherein the compound is labeled with one or more positron-emitting radionuclides. In some embodiments, the compound contains one or more positron-emitting radionuclides selected from $^{11}C$, $^{13}N$, $^{15}O$, and $^{18}F$.

Also provided is a method of generating diagnostic images, for example positron emission tomography (PET) images, in an individual comprising administering an effective amount of a compound described herein or an imaging agent comprising a compound described herein, and generating an image of a body part or body area of the individual.

In some embodiments, provided is a compound or an imaging agent for use in generating diagnostic images in an individual, wherein the use comprises administering an effective amount of a compound or an imaging agent described herein to an individual, and generating an image of a body part or body area of the individual.

In some embodiments, provided is a compound or an imaging agent for use as described herein, wherein generating an image of a body part or body area of the individual comprises generating an image to detect the presence or absence of a protein susceptible to aggregation in the image. In some embodiments, provided is a compound or an imaging agent for use as described herein, wherein the protein susceptible to aggregation is huntingtin protein (HTT protein). In some embodiments, provided is a compound or an imaging agent for use as described herein, wherein the HTT protein is found in basal ganglia.

In some embodiments, provided is a compound or an imaging agent for use as described herein, wherein the presence or absence of a protein aggregate corresponds to the presence or absence of a neurodegenerative disease.

In some embodiments, provided is a compound or an imaging agent for use as described herein, wherein the neurodegenerative disease is selected from Alzheimer's disease, amyotrophic lateral sclerosis, Huntington's disease, Parkinson's disease, Prion disease and spinocerebellar ataxias. In some embodiments, provided is a compound or an imaging agent for use as described herein, wherein the neurodegenerative disease is Huntington's disease (HD).

In some embodiments, provided is a compound or an imaging agent for use as described herein, wherein the effective amount of the imaging agent comprises from about 0.1 to about 20 mCi. In some embodiments, provided is a compound or an imaging agent for use as described herein, wherein the effective amount of the imaging agent comprises about 10 mCi.

In some embodiments, provided is a compound or an imaging agent for use as described herein, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, provided is a compound or an imaging agent for use as described herein, wherein generating an image comprises PET imaging.

In some embodiments, provided is a compound or an imaging agent for use as described herein, wherein the HTT protein is present as oligomers or aggregates, or a combination thereof. In some embodiments, provided is a compound or an imaging agent for use as described herein, wherein the HTT protein is mutant.

In some embodiments, provided is a compound or an imaging agent for use as described herein, wherein the body part or body area is head, spinal cord, limb, thorax, or abdomen. In some embodiments, provided is a compound or an imaging agent for use as described herein, wherein the body part or body area is a brain.

DETAILED DESCRIPTION

The following description sets forth exemplary embodiments of the present technology. It should be recognized, however, that such description is not intended as a limitation on the scope of the present disclosure but is instead provided as a description of exemplary embodiments.

Definitions

As used in the present specification, the following words, phrases and symbols are generally intended to have the meanings as set forth below, except to the extent that the context in which they are used indicates otherwise.

A compound described herein refers to a compound, or an isotopically labeled analog, pharmaceutically acceptable salt, solvate, prodrug, stereoisomer, or mixture of stereoisomers thereof, of any formula described herein, including those of Formula I, Formula II, Formula III, Formula IV, Formula V, Formula VI, Formula VII, Formula VIII, Formula IX, or a compound described anywhere herein including the Examples, or a compound of Table 1 or a labeled isomer of such compound as defined herein, or an imaging agent or pharmaceutical composition comprising such compound or labeled compound.

A dash ("-") that is not between two letters or symbols is used to indicate a point of attachment to a parent structure for a substituent. For example, —C(O)NH$_2$ is attached to a parent structure through the carbon atom. A dash at the front or end of a chemical group is a matter of convenience; chemical groups may be depicted with or without one or more dashes without losing their ordinary meaning. A wavy line or a dashed line drawn through a bond in a structure indicates a specified point of attachment. Unless chemically or structurally required, no directionality or stereochemistry is indicated or implied by the order in which a chemical group is written or named.

The prefix "$C_{u-v}$" indicates that the following group has from u to v carbon atoms, exclusive of further substitution. For example, "$C_{1-6}$ alkyl" indicates an alkyl group having from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount 1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 9 carbon atoms (i.e., $C_{1-9}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Alternative chemical names known to those of skill in the art may be used in lieu of the terms provided herein. For example, a divalent group such as a divalent "alkyl" group, a divalent "aryl" group, etc., may also be referred to as an "alkylene" or an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl), and isoprenyl.

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to a group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylamino" refers to a group "alkyl-NH—". Examples of alkylamino groups include, e.g., methylamino, ethylamino, iso-propylamino, tert-butylamino, and n-hexylamino. "Dialkylamino" refers to a group "(alkyl)$_2$N—". Examples of dialkylamino groups include, e.g., dimethylamino, diethylamino, (iso-propyl)(methyl)amino, (n-pentyl)(tert-butyl)amino, and di-n-hexylamino.

"Alkylthio" refers to a group "alkyl-S—". "Alkylsulfinyl" refers to the group "alkyl-S(O)—". "Alkylsulfonyl" refers to a group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethylcarbonyl and benzoyl.

"Amido" refers to both a "C-amido" group which refers to a group —C(O)NR$^y$R$^z$ and an "N-amido" group which refers to a group —NR$^y$C(O)R$^z$, wherein R$^y$ and R$^z$ are independently hydrogen, alkyl, alkenyl, alkynyl, haloalkyl, cycloalkyl, heterocyclyl, aryl, heteroalkyl or heteroaryl; each of which may be optionally substituted, as defined herein, or $R^y$ and $R^z$ are taken together to form a cycloalkyl or heterocyclyl; each of which may be optionally substituted, as defined herein.

"Amino" refers to a group —$NR^yR^z$ wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein. In some embodiments, "amino" refers to a group $NH_2$.

"Amidino" refers to a group —$C(NR^y)(NR^z_2)$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl) or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to a group "aryl-alkyl-".

"Carbamoyl" refers to both an "O-carbamoyl" group which refers to a group —O—$C(O)NR^yR^z$ and an "N-carbamoyl" group which refers to a group —$NR^yC(O)OR^z$, wherein $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Carboxyl ester" or "ester" refer to both —$OC(O)R^x$ and —$C(O)OR^x$, wherein $R^x$ is alkyl, alkenyl, alkynyl, haloalkyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp3 ring carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cyclohexenyl, cycloheptyl and cyclooctyl. Polycyclic groups include, for example, bicyclo[2.2.1]heptanyl, bicyclo[2.2.2]octanyl, adamantyl, norbornyl, norbornenyl, decalinyl, 7,7-dimethyl-bicyclo[2.2.1]heptanyl and the like. Further, the term cycloalkyl is intended to encompass any non-aromatic ring system which may include a fused aryl ring, regardless of the attachment to the remainder of the molecule. Still further, cycloalkyl also includes "spirocycloalkyl," for example spiro[2.5]octanyl, spiro[4.5]decanyl, or spiro[5.5]undecanyl. When there are two positions for substitution on a carbon atom in a parent structure, cycloalkyl as a substituent group may include spirocycloalkyl. A cycloalkyl may be substituted at its carbon atom of attachment to a parent structure.

"Cycloalkoxy" refers to a group "—O-cycloalkyl."

"Cycloalkylalkyl" refers to a group "cycloalkyl-alkyl-".

"Guanidino" refers to —$NR^yC(=NR^z)(NR^yR^z)$, wherein each $R^y$ and $R^z$ are independently hydrogen, alkyl, alkenyl, alkynyl, haloalkyl, cycloalkyl, heterocyclyl, aryl, heteroalkyl or heteroaryl; each of which may be optionally substituted, as defined herein.

"Imino" refers to a group —$C(NR^y)R^z$, wherein $R^y$ and $R^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Imido" refers to a group —$C(O)NR^yC(O)R^z$, wherein $R^y$ and $R^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

"Halogen" or "halo" refers to a substituent atom of group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms, up to and including all hydrogen atoms, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. A perhaloalkyl group is a haloalkyl group in which every hydrogen substituent is replaced by halo. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms, up to and including all hydrogen atoms, are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms of the alkyl chain (and any associated hydrogen atoms) are each independently replaced with the same or different heteroatomic group, provided the point of attachment to the remainder of the molecule is through a carbon atom. The term "heteroalkyl" includes unbranched or branched saturated chains having carbon and heteroatoms. By way of example, 1, 2 or 3 carbon atoms may be independently replaced with the same or different heteroatomic group. Heteroatomic groups include, but are not limited to, —$NR^y$—, —$C(O)NR^y$—, —$NR^yC(O)$—, —O—, —S—, —$S(O)$—, —$S(O)_2$—, and the like, wherein $R^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.) and aminoalkyls (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, haloalkyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring or multiple fused rings, with one or more ring heteroatoms independently selected from nitrogen, oxygen, and sulfur, and may comprise one or more (e.g., 1 to 3) N-oxide (—O⁻) moieties. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring system, having a single or multiple fused rings containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to a group "heteroaryl-alkyl-".

"Heterocyclyl" refers to a saturated or partially unsaturated cyclic alkyl group, with one or more ring heteroatoms independently selected from nitrogen, oxygen and sulfur, wherein the nitrogen or sulfur atoms are optionally oxidized to form an N-oxide, a sulfinyl (—S(O)—), or a sulfoxide (—S(O)₂—). The term "heterocyclyl" includes heterocycloalkenyl groups (i.e., a heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro. Regardless of substituent groups listed, a heterocyclyl may comprise one or more (e.g., 1 to 3) oxo (═O) or N-oxide (—O⁻) moieties unless stated otherwise. A heterocyclyl can be bound through a carbon atom or a heteroatom as valency permits. Further, the term heterocyclyl encompasses any ring system including a non-aromatic ring containing at least one heteroatom, which ring may be fused to an aryl or heteroaryl ring, regardless of the attachment to the remainder of the molecule. A heterocyclyl may have a charged resonance structure that is aromatic (e.g., pyridin-2(1H)-on-1-yl). As used herein, a heterocyclyl may include 3 to 14 ring atoms, 3 to 10 ring atoms, 3 to 6 ring atoms, or 5 to 6 ring atoms, and/or 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl." Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. When there are two positions for substitution on a carbon atom in a parent structure, heterocyclyl as a substituent group may include spiroheterocyclyl. Examples of bridged-heterocyclyl rings include, but are not limited to, 2,5-diazabicyclo[2.2.1]heptane, 2-oxa-5-azabicyclo[2.2.1]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. An "oxo-heterocyclyl" group is a heterocyclyl including at least one oxo substituent (e.g., 1, or 1 to 2 oxo substituents), whether or not additional substituents are permitted (i.e., an unsubstituted oxo-heterocyclyl includes an oxo and no other substitution). In some embodiments, an oxo-heterocyclyl includes a cyclic amide moiety.

"Heterocyclylalkyl" refers to a group "heterocyclyl-alkyl-."

"Oxime" refers to a group —CR$^y$(═NOH) wherein R$^y$ is hydrogen, alkyl, alkenyl, alkynyl, haloalkyl, cycloalkyl, heterocyclyl, aryl, heteroalkyl or heteroaryl; each of which may be optionally substituted, as defined herein.

"Sulfonyl" refers to a group —S(O)₂R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to a group —S(O)R$^y$, where R$^y$ is hydrogen, alkyl, alkenyl, alkynyl, haloalkyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO₂NR$^y$R$^z$ and —NR$^y$SO₂R$^z$, where R$^y$ and R$^z$ are each independently hydrogen, alkyl, alkenyl, alkynyl, haloalkyl, cycloalkyl, heterocyclyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to a group which is unsubstituted or substituted.

The term "substituted" used herein refers to a group in which any one or more (e.g., 1 to 5 or 1 to 3) hydrogen atoms is replaced by a non-hydrogen group such as, but not limited to alkyl, alkenyl, alkynyl, alkoxy, alkylthio, acyl, amido, amino, amidino, aryl, arylalkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, haloalkyl, heteroalkyl, cycloalkyl, aryl, heteroaryl, or heterocyclyl.

In certain embodiments, "substituted" refers to a group in which one or more (e.g., 1 to 5 or 1 to 3) hydrogen atoms are independently replaced with deuterium, halo, cyano, hydroxyl, imino, nitro, azido, oxo, thioxo, alkyl, alkenyl, alkynyl, haloalkyl, alkoxy, thioalkyl, haloalkoxy, cycloalkyl, heterocyclyl, N-heterocyclyl, heterocyclylalkyl, aryl, arylalkyl, heteroaryl, heteroarylalkyl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, or —SCF$_3$. In certain embodiments, "substituted" also means a group in which one or more (e.g., 1 to 5 or 1 to 3) hydrogen atoms are replaced with —C(=O)R$^g$, —C(=O)OR$^g$, —C(=O)NR$^g$R, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, arylalkyl, cycloalkyl, cycloalkylalkyl, haloalkyl, heterocyclyl, heterocyclylalkyl, heteroaryl, and/or heteroarylalkyl, or R$^g$ and R$^h$ are taken together with the atoms to which they are attached to form a heterocyclyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended to arise from the above definitions. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to encompass compounds having chemically unfeasible or unisolable substitution patterns (e.g., methyl substituted with 5 fluorines or heteroaryl groups having three consecutive oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein is intended to represent unlabeled forms as well as "isotopically enriched analogs" of the compounds. Isotopically enriched forms of compounds may also be referred to as "labeled." Isotopically enriched analogs have structures depicted herein, except that one or more atoms are enriched in an isotope having a selected atomic mass or mass number. Examples of isotopes that can be incorporated into the compounds described herein include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Generally, an isotopically enriched analog includes compounds having any isotopic enrichment above the natural abundance of the isotope (e.g., at Earth's surface). Various isotopically labeled compounds are included in the present disclosure, for example those into which radioactive isotopes such as $^3$H, $^{18}$F, $^{11}$C, and $^{14}$C are incorporated. Compounds labeled with $^{18}$F, $^3$H, or $^{11}$C may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and thus may be useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Isotopically labeled compounds of this disclosure and pharmaceutically acceptable salts, prodrugs, tautomers, stereoisomers, and mixtures of stereoisomers thereof can generally be prepared by carrying out the procedures disclosed in the schemes or in the examples and preparations described below by substituting a readily available isotopically labeled reagent for a non-isotopically labeled reagent. Where a compound is described as a deuterated analog, the compound may be drawn with deuterium as a substituent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen and its isotopes at their natural abundances.

In many cases, the compounds of this disclosure are capable of forming acid and/or base salts by virtue of the presence of amino and/or carboxyl groups or groups similar thereto.

Provided also are isotopically enriched analogs, pharmaceutically acceptable salts, prodrugs, tautomers, stereoisomers, and mixtures of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a compound described herein refers to salts that retain the biological effectiveness and properties of the given compound and which are not biologically or otherwise undesirable. "Pharmaceutically acceptable salts" or "physiologically acceptable salts" of compounds described herein include, for example, acid addition salts obtained by interacting a compound with a basic functional group with an acid, and base addition salts obtained by interacting a compounds with an acidic functional group with a base. If the compound is obtained as an acid addition salt, the free base can be obtained by basifying a solution of the acid salt. Conversely, if the compound is a free base (e.g., of an amine), an addition salt may be produced by dissolving the free base in a suitable organic solvent and treating the solution with an acid. Those skilled in the art will recognize various synthetic methodologies that may be used to prepare nontoxic pharmaceutically acceptable addition salts. Pharmaceutically acceptable acid addition salts of compounds described herein may be prepared from inorganic and organic acids. Suitable inorganic acids include, e.g., hydrochloric acid, hydrobromic acid, sulfuric acid, nitric acid, phosphoric acid and the like. Suitable organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$ (substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), cyclic amines (e.g., piperidine, piperazine, 1,4-diazabicyclo[2.2.2]octane), aromatic amines (e.g., pyridine, quinoline), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some compounds described herein may exist as tautomers. For example, where a compound is drawn as including an amide, the compound may exist as an imidic acid tautomer, and where a compound is drawn as including a ketone, the compound may also exist as an enol tautomer. Regardless of which tautomer is shown and regardless of the nature of the equilibrium among tautomers, the compounds are understood by one of ordinary skill in the art to comprise both tautomers. Thus, for example, the amide containing compounds are understood to include their imidic acid tautomers, and the imidic acid containing compounds are understood to include their amide tautomers.

The compounds described herein may include an asymmetric center and may thus give rise to enantiomers, diastereomers, and other stereoisomeric forms that may be defined, in terms of absolute stereochemistry, as (R)- or (S)-, or as (D)- or (L)- for amino acids. Compounds described herein are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain double bonds or other centers of geometric asymmetry, and unless specified otherwise, it is intended that the compounds include both cis- and trans- or E- and Z-geometric isomers.

A "stereoisomer" refers to one of a set of compounds made up of the same atoms bonded by the same bonds but having different three-dimensional structures. Various stereoisomers and mixtures thereof are contemplated including "enantiomers," which refers to stereoisomeric compounds that are non-superimposable mirror images of one another.

A "diastereomer" is one of a set of stereoisomers that have at least two asymmetric atoms that are not mirror-images of each other.

A "prodrug" is any molecule which releases a putatively active parent drug according to a compound described herein in vivo when such prodrug is administered to a mammalian subject. A prodrug may be a form of a compound described herein modified in such a way that the modifications may be cleaved in vivo to release the parent compound. Prodrugs may be prepared by modifying functional groups present in the compound described herein in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

In some embodiments, the term "neurodegenerative disease" refers to a disease or condition in which the function of a subject's nervous system becomes impaired. Examples of neurodegenerative diseases include those described herein.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The above-listed terms also include in vitro and ex vivo methods.

As used herein the terms "group," "moiety," "radical," "substituent," and "fragment" are synonymous and are intended to indicate portions of molecules attachable to other portions of molecules, e.g., through an indicated attachment point or bond.

The term "active agent" is used to indicate a compound which has biological activity in the treatment, amelioration, or prevention of a disease or condition. In some embodiments, an "active agent" is a compound or an isotopically labeled analog, pharmaceutically acceptable salt, solvate, prodrug, stereoisomer, or mixture of stereoisomers thereof, having pharmaceutical utility. For example, an active agent may be an anti-neurodegenerative therapeutic.

The term "effective amount" means an amount, for example, of a compound described herein, sufficient to bring about a desired response in an individual or patient. In the context of use of an imaging agent, an effective amount may be an amount needed to produce an image having diagnostic or therapeutic utility. The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease described herein. The (therapeutically) effective amount may vary depending on the subject, and disease or condition being treated, the weight and age of the subject, the severity of the disease or condition, and the manner of administering, which can readily be determined by one of ordinary skill in the art.

The term "huntingtin protein" or "HTT protein" as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "protein aggregate," as used herein refers to an aggregation of protein which may be, for example, an insoluble fibrous amyloid comprising mis-folded HTT protein molecules ("HTT protein aggregate") or mis-folded β-amyloid protein molecules ("β-amyloid aggregate"). A "protein susceptible to aggregation" is a protein that is capable of forming such aggregates, in its wild type or in a mutated form.

The term "imaging agent," as used herein, refers to a compound described herein labeled with one or more positron-emitting isotopes or radionuclides, or a composition comprising the labeled compound. A positron-emitter labeled compound need only be enriched with a detectable isotope to a degree that permits detection with a technique suitable for the particular application.

The term "PET imaging" (which may be referred to as positron emission tomography imaging), as used herein, refers to the use of a positron-emitter labeled compound to produce images of internal structures of the human or animal body.

The term "positron-emitting radionuclide," as used herein, refers to a radioactive isotope that exhibits a particular type of radioactive decay referred to as β+ decay, in which a proton inside a radionuclide nucleus is converted into a neutron while releasing a positron and an electron neutrino (ve). Some examples of positron-emitting radionuclides include $^{15}O$, $^{13}N$, $^{11}C$, $^{18}F$, $^{76}Br$, and $^{124}I$.

The term "labeled," as used herein, refers to a compound which is associated with one or more positron-emitting radionuclides in greater than natural abundance. For example, a labeled compound described herein may contain one or more positron-emitting radionuclides, wherein an atom in the molecule (including any indicated substituent) is present as a positron-emitting isotope.

The term "tomography," as used herein, refers to a process of imaging by sections. The images may be looked at individually, as a series of two-dimensional slices or together, as a computer-generated three-dimensional representation.

In some embodiments, the term "neurodegenerative disease" refers to a disease or condition in which the function of a subject's nervous system becomes impaired. Examples of neurodegenerative diseases include those described herein.

"Treatment" or "treating" means any treatment of a disease state in a patient, including a) inhibiting the disease (e.g., decreasing one or more symptoms resulting from the disease or condition, and/or diminishing the extent of the disease or condition);

b) slowing or arresting the development of clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in some embodiments, be administered to a subject (including a human) who is at risk (e.g., carries a genetic or epigenetic marker, has engaged in an activity, or has been exposed to an environmental condition, associated with the disease or condition) or has a family history of the disease or condition.

"Subject" or "patient" refers to an animal, such as a mammal, that has been or will be the object of treatment, observation or experiment. The methods described herein may be useful in both human therapy and veterinary applications. In some embodiments, the subject or patient is a mammal. In some embodiments the subject or patient is human.

The term "Curie" (Ci) is a unit of measurement of radioactivity and has its customary meaning to those of skill in the art.

The term "diagnostic imaging," as used herein, refers to the use of electromagnetic radiation to produce images of internal structures of the human or animal body for the purpose of diagnosis.

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I or any other formula are specifically embraced herein just as if each and every combination was individually and explicitly recited, to the extent that such combinations result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced herein just as if each and every subcombination of chemical groups and subcombination of uses and medical indications was individually and explicitly recited herein. In addition, some embodiments include every combination of one or more additional agents disclosed herein just as if each and every combination was individually and explicitly recited.

| List of Abbreviations and Acronyms | |
|---|---|
| δ | Chemical shift |
| μ | Micro |
| Ac | Acetate |
| addn. | Addition |
| approx. | Approximately |
| aq | Aqueous |
| Ar | Aryl |
| atm | Atmosphere |
| Bn | Benzyl |
| Boc | Tert-butyloxycarbonyl |
| br | Broad |
| Bz | Benzoyl |
| conc. | Concentrated |
| d | Deuterated |
| d | Doublet |
| dd | Doublet of doublets |
| dba | Dibenzylideneacetone |
| DCM | Dichloromethane |
| DIPEA | Diisopropylethylamine |
| dppf | Bisdiphenylphosphinyl ferrocene |

| List of Abbreviations and Acronyms | |
|---|---|
| DMF | N,N-dimethylformamide |
| DMSO | Dimethyl sulfoxide |
| EDC | 1-Ethyl-3-(3-dimethylaminopropyl)carbodiimide |
| ELS | Evaporative light scattering |
| eq | Equivalent |
| ES | Electrospray ionization |
| Et | Ethyl |
| EtOAc | Ethyl acetate |
| EtOH | Ethanol |
| FCC | Flash column chromatography |
| h | Hour(s) |
| HATU | N-[(Dimethylamino)-1H-1,2,3-triazolo-[4,5-b]pyridin-1-ylmethylene]-N-ethylmethanaminium hexafluorophosphate N-oxide |
| HPLC | High performance liquid chromatography |
| LCMS | Liquid chromatography-mass spectrometry |
| IPA | Isopropyl alcohol |
| J | Coupling constant |
| m | Multiplet |
| Me | Methyl |
| MeCN | Acetonitrile |
| MeOH | Methanol |
| m/z | Mass to charge ratio |
| N | Normal |
| NMR | Nuclear magnetic resonance |
| p | Para |
| Ph | Phenyl |
| ppm | Part(s) per million |
| q | Quartet |
| quant. | Quantitative |
| rt | Room temperature |
| s | Singlet |
| sat. | Saturated |
| SCX | Propylsulfonic acid (non-endcapped) functionalized silica |
| t | Triplet |
| THF | Tetrahydrofuran |
| Tr | Retention time |
| Ts | p-Toluenesulfonyl |
| UV | Ultraviolet |

Compounds

The present disclosure relates to compounds useful for imaging a protein susceptible to aggregation, for example, huntingtin protein. Some embodiments provide a compound of Formula I:

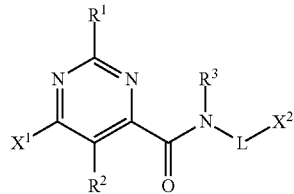

or an isotopically enriched analog, pharmaceutically acceptable salt, prodrug, tautomer, stereoisomer, or a mixture of stereoisomers thereof, wherein the compound is labeled with one or more radioactive isotopes;

wherein:

$R^1$ is hydrogen, halo, $C_{1-6}$alkyl, $C_{1-6}$haloalkyl, $C_{1-6}$alkoxy, $C_{1-6}$haloalkoxy, or phenyl;

$R^2$ is hydrogen, halo, $C_{1-6}$alkyl, $C_{1-6}$haloalkyl, $C_{1-6}$alkoxy, or $C_{1-6}$haloalkoxy;

$R^3$ is hydrogen, $C_{1-6}$alkyl, or $C_{1-6}$haloalkyl;

$X^1$ is $C_{6-10}$aryl or heteroaryl, each of which is optionally substituted with 1 to 4 $R^4$;

$X^2$ is heteroaryl, heterocyclyl, or oxo-heterocyclyl, each of which is optionally substituted with 1 to 4 $R^6$;

each $R^4$ is independently halo, cyano, hydroxy, nitro, amino, alkylamino, dialkylamino, $C_{1-6}$alkyl optionally substituted with $R^5$, $C_{1-6}$haloalkyl, $C_{1-6}$hydroxyalkyl, $C_{1-6}$alkoxy optionally substituted with $R^5$, or $C_{1-6}$haloalkoxy;

each $R^5$ is independently halo, cyano, hydroxy, amino, alkylamino, dialkylamino, or $C_{1-6}$alkoxy;

each $R^6$ is independently halo, cyano, hydroxy, nitro, amino, alkylamino, dialkylamino, $C_{1-6}$alkyl optionally substituted with $R^7$, $C_{1-6}$haloalkyl, $C_{1-6}$hydroxyalkyl, $C_{1-6}$alkoxy optionally substituted with $R^7$, or $C_{1-6}$haloalkoxy;

each $R^7$ is independently halo, cyano, hydroxy, amino, alkylamino, dialkylamino, or $C_{1-6}$alkoxy;

L is $(C(R^8)_2)_n$;

n is 0, 1, or 2;

each $R^8$ is independently hydrogen, halo, $C_{1-6}$alkyl, $C_{1-6}$haloalkyl or $C_{1-6}$alkoxy;

or one of $R^3$ or $R^8$, together with the intervening atoms, forms a 3- to 6-membered saturated or partially unsaturated ring with $R^6$.

In some embodiments, provided is a compound of Formula I:

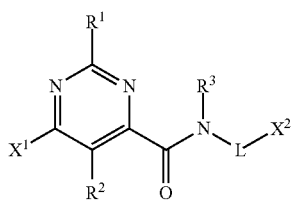

or an isotopically enriched analog, pharmaceutically acceptable salt, prodrug, tautomer, stereoisomer, or a mixture of stereoisomers thereof, wherein:

$R^1$ is hydrogen, halo, $C_{1-6}$alkyl, $C_{1-6}$haloalkyl, $C_{1-6}$alkoxy, $C_{1-6}$haloalkoxy, or phenyl;

$R^2$ is hydrogen, halo, $C_{1-6}$alkyl, $C_{1-6}$haloalkyl, $C_{1-6}$alkoxy, or $C_{1-6}$haloalkoxy;

$R^3$ is hydrogen, $C_{1-6}$alkyl, or $C_{1-6}$haloalkyl;

$X^1$ is $C_{6-10}$aryl or heteroaryl, each of which is optionally substituted with 1 to 4 $R^4$;

$X^2$ is oxo-heterocyclyl optionally substituted with 1 to 4 $R^6$;

each $R^4$ is independently halo, cyano, hydroxy, nitro, amino, alkylamino, dialkylamino, $C_{1-6}$alkyl optionally substituted with $R^5$, $C_{1-6}$haloalkyl, $C_{1-6}$hydroxyalkyl, $C_{1-6}$alkoxy optionally substituted with $R^5$, or $C_{1-6}$haloalkoxy;

each $R^5$ is independently halo, cyano, hydroxy, amino, alkylamino, dialkylamino, or $C_{1-6}$alkoxy;

each $R^6$ is independently halo, cyano, hydroxy, nitro, amino, alkylamino, dialkylamino, $C_{1-6}$alkyl optionally substituted with $R^7$, $C_{1-6}$haloalkyl, $C_{1-6}$hydroxyalkyl, $C_{1-6}$alkoxy optionally substituted with $R^7$, or $C_{1-6}$haloalkoxy;

each $R^7$ is independently halo, cyano, hydroxy, amino, alkylamino, dialkylamino, or $C_{1-6}$alkoxy;

L is $(C(R^8)_2)_n$;

n is 0, 1, or 2; and each $R^8$ is independently hydrogen, halo, $C_{1-6}$alkyl, $C_{1-6}$haloalkyl or $C_{1-6}$alkoxy;

or one of $R^3$ or $R^8$, together with the intervening atoms, forms a 3- to 6-membered saturated or partially unsaturated ring with $R^6$;

provided that the compound is not 6-(3,4-Dichloro-phenyl)-pyrimidine-4-carboxylic acid (5-oxo-pyrrolidin-2-yl)-amide.

In some embodiments, the compound of Formula I is a compound of Formula II:

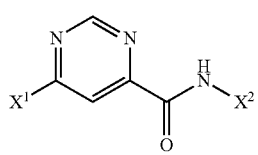

or an isotopically enriched analog, pharmaceutically acceptable salt, prodrug, tautomer, stereoisomer, or a mixture of stereoisomers thereof.

In some embodiments, the compound of Formula I is a compound of Formula III:

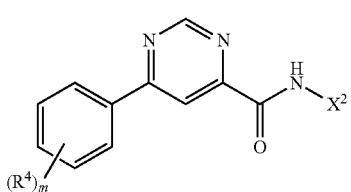

or an isotopically enriched analog, pharmaceutically acceptable salt, prodrug, tautomer, stereoisomer, or a mixture of stereoisomers thereof;

wherein m is 0 to 4.

In some embodiments, the compound of Formula I is a compound of Formula IV:

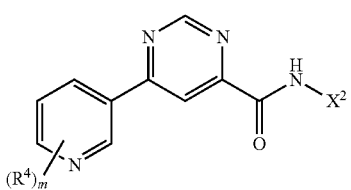

or an isotopically enriched analog, pharmaceutically acceptable salt, prodrug, tautomer, stereoisomer, or a mixture of stereoisomers thereof;

wherein m is 0 to 4.

In some embodiments, the compound of Formula I is a compound of Formula V:

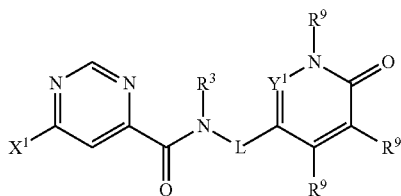

V or an isotopically enriched analog, pharmaceutically acceptable salt, prodrug, tautomer, stereoisomer, or a mixture of stereoisomers thereof; wherein $Y^1$ is N or $CR^9$, and each $R^9$ is independently hydrogen or $R^6$.

In some embodiments, the compound of Formula I is a compound of Formula VI:

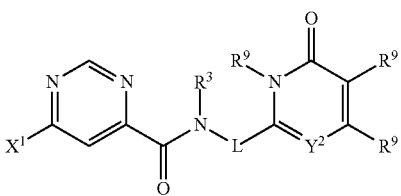

VI or an isotopically enriched analog, pharmaceutically acceptable salt, prodrug, tautomer, stereoisomer, or a mixture of stereoisomers thereof; wherein $Y^2$ is N or $CR^9$, and each $R^9$ is independently hydrogen or $R^6$.

In some embodiments, the compound of Formula I is a compound of Formula VII:

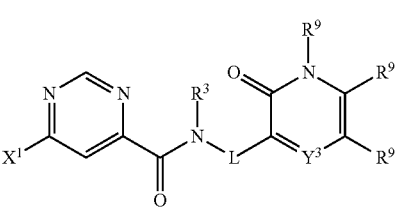

VII or an isotopically enriched analog, pharmaceutically acceptable salt, prodrug, tautomer, stereoisomer, or a mixture of stereoisomers thereof; wherein $Y^3$ is N or $CR^9$, and each $R^9$ is independently hydrogen or $R^6$.

In some embodiments, the compound of Formula I is a compound of Formula VIII:

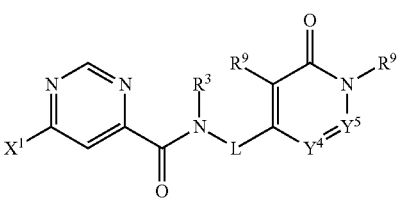

VIII or an isotopically enriched analog, pharmaceutically acceptable salt, prodrug, tautomer, stereoisomer, or a mixture of stereoisomers thereof; wherein one of $Y^4$ and $Y^5$ is N and the other is $CR^9$, wherein each $R^9$ is independently hydrogen or $R^6$.

In some embodiments, the compound of Formula I is a compound of Formula IX:

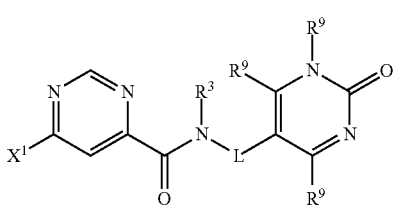

IX or an isotopically enriched analog, pharmaceutically acceptable salt, prodrug, tautomer, stereoisomer, or a mixture of stereoisomers thereof; wherein each $R^9$ is independently hydrogen or $R^6$.

In some embodiments, $X^2$ is oxo-heterocyclyl.

In some embodiments, $X^2$ is

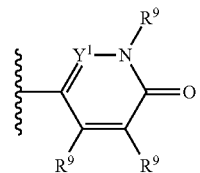

wherein $Y^1$ is N or $CR^9$, and each $R^9$ is independently hydrogen or $R^6$.

In some embodiments, $X^2$ is

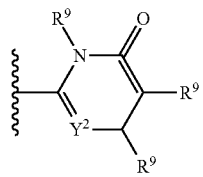

wherein $R^9$ wherein $Y^2$ is N or $CR^9$, and each $R^9$ is independently hydrogen or $R^6$.

In some embodiments, $X^2$ is

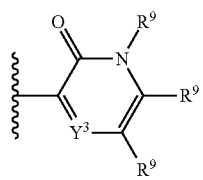

wherein $Y^3$ is N or $CR^9$, and each $R^9$ is independently hydrogen or $R^6$.

In some embodiments, $X^2$ is

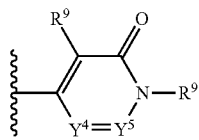

wherein one of $Y^4$ and $Y^5$ is N and the other is $CR^9$, wherein each $R^9$ is independently hydrogen or $R^6$.

In some embodiments, $X^2$ is

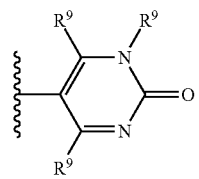

wherein each $R^9$ is independently hydrogen or $R^6$.

In some embodiments, $X^2$ is 6-oxo-1,6-dihydropyridazin-3-yl, 6-oxo-1,6-dihydropyrimidin-2-yl, 6-oxo-1,6-dihydropyridin-3-yl, 3-oxo-3,4-dihydropyrazin-2-yl, 6-oxo-1,6-dihydropyridazin-4-yl, or 6-oxo-1,6-dihydropyrimidin-4-yl.

In some embodiments, $X^2$ is

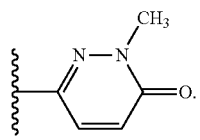 [SMILES: *c1ccc(=O)n(C)n1]

In some embodiments, $X^2$ is heteroaryl.

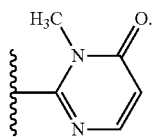 [SMILES: *c1nccc(=O)n1C]

In some embodiments, $X^2$ is pyridinyl, pyrazinyl, pyridazinyl, or pyrimidinyl.

In some embodiments, $X^2$ is N

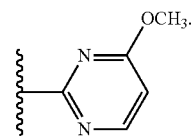

In some embodiments, $X^1$ is phenyl. In some embodiments, $X^1$ is unsubstituted phenyl.

In some embodiments, $X^1$ is phenyl optionally substituted with 1 or 2 $R^4$. In some embodiments, $X^1$ is phenyl substituted with 1 or 2 $R^4$. In some embodiments, $X^1$ is phenyl substituted with 1 $R^4$. In some embodiments, $X^1$ is phenyl substituted with 2 $R^4$.

In some embodiments, $X^1$ is heteroaryl. In some embodiments, $X^1$ is heteroaryl optionally substituted with 1 or 2 $R^4$. In some embodiments, $X^1$ is heteroaryl substituted with 1 or 2 $R^4$.

In some embodiments, $X^1$ is pyridinyl. In some embodiments, $X^1$ is pyridin-2-yl. In some embodiments, $X^1$ is pyridin-3-yl.

In some embodiments, $X^1$ is pyrimidinyl. In some embodiments, $X^1$ is pyrimidin-2-yl. In some embodiments, $X^1$ is pyrimidin-5-yl.

In some embodiments, $X^1$ is pyrazinyl. In some embodiments, $X^1$ is pyrazin-2-yl.

In some embodiments, $R^1$ is hydrogen.
In some embodiments, $R^2$ is hydrogen.
In some embodiments, $R^3$ is hydrogen.
In some embodiments, each $R^4$ is independently halo, cyano, $C_{1-6}$alkyl, or $C_{1-6}$alkoxy. In some embodiments, each $R^4$ is independently halo, cyano, $C_{1-3}$alkyl, or $C_{1-3}$alkoxy.

In some embodiments, $R^4$ is halo. In some embodiments, $R^4$ is fluoro or chloro. In some embodiments, $R^4$ is fluoro. In some embodiments, $R^4$ is chloro.

In some embodiments, $R^4$ is $C_{1-6}$alkoxy. In some embodiments, $R^4$ is $C_{1-3}$alkoxy. In some embodiments, $R^4$ is methoxy.

In some embodiments, $R^4$ is cyano.

In some embodiments, each $R^6$ is independently halo, $C_{1-6}$alkyl, or $C_{1-6}$alkoxy. In some embodiments, each $R^6$ is independently halo, $C_{1-3}$alkyl, or $C_{1-3}$alkoxy.

In some embodiments, n is 0. In some embodiments, n is 1. In some embodiments, n is 1 and each $R^8$ is hydrogen.

In some embodiments, m is 1, 2, or 3. In some embodiments, m is 1 or 2. In some embodiments, m is 1. In some embodiments, m is 2.

In some embodiments, provided is a compound selected from those in Table 1, or an isotopically enriched analog, pharmaceutically acceptable salt, prodrug, tautomer, stereoisomer, or a mixture of stereoisomers thereof, optionally wherein the compound is labeled with one or more radioactive isotopes.

In some embodiments, the compound of Formula I is not N-[6-(3-Chloro-phenyl)-pyrimidin-4-yl]-nicotinamide, 6-(3,4-Dichloro-phenyl)-2-methyl-pyrimidine-4-carboxylic acid pyridin-3-ylamide, 6-(3-Chloro-phenyl)-pyrimidine-4-carboxylic acid (2,6-dimethyl-pyridin-3-yl)-amide, 6-(3-Chloro-phenyl)-pyrimidine-4-carboxylic acid pyrimidin-5-ylamide, 6-(3-Trifluoromethyl-phenyl)-pyrimidine-4-carboxylic acid pyridin-2-ylamide, 6-(4-Fluoro-3-trifluoromethyl-phenyl)-pyrimidine-4-carboxylic acid pyridin-3-ylamide, 6-(3,5-Dichloro-phenyl)-pyrimidine-4-carboxylic acid pyridin-3-ylamide, 6-(3-Trifluoromethyl-phenyl)-pyrimidine-4-carboxylic acid pyridin-3-ylamide, [6-(3-Chloro-phenyl)-pyrimidin-4-yl]-(3,4-dihydro-2H-quinolin-1-yl)-methanone, 6-(3-Chloro-phenyl)-pyrimidine-4-carboxylic acid (6-methoxy-pyridin-3-yl)-amide, [6-(3-Chloro-phenyl)-pyrimidin-4-yl]-(2,3-dihydro-indol-1-yl)-methanone, 6-(3-Chloro-phenyl)-pyrimidine-4-carboxylic acid methyl-pyridin-3-yl-amide, 6-(3-Chloro-phenyl)-pyrimidine-4-carboxylic acid (5-methoxy-pyridin-3-yl)-amide, 6-Phenyl-pyrimidine-4-carboxylic acid pyridin-3-ylamide, 6-(3-Chloro-phenyl)-pyrimidine-4-carboxylic acid (4-methoxy-pyridin-3-yl)-amide, 6-(3-Chloro-phenyl)-2-methyl-pyrimidine-4-carboxylic acid pyridin-3-ylamide, [6-(3,4-Dichloro-phenyl)-pyrimidin-4-yl]-(2,3-dihydro-indol-1-yl)-methanone, 6-(3-Chloro-phenyl)-pyrimidine-4-carboxylic acid pyridin-2-ylamide, 6-(3-Chloro-phenyl)-pyrimidine-4-carboxylic acid pyridin-4-ylamide, 6-(3-Chloro-phenyl)-pyrimidine-4-carboxylic acid (pyridin-4- ylmethyl)-amide, 6-(3-Chloro-phenyl)-pyrimidine-4-carboxylic acid [1,3,4]thiadiazol-2-ylamide, 6-(3-Chloro-phenyl)-pyrimidine-4-carboxylic acid isoxazol-3-ylamide, 6-(3-Chloro-phenyl)-pyrimidine-4-carboxylic acid (6-trifluoromethyl-pyridin-3-yl)-amide, 6-(3-Chloro-phenyl)-pyrimidine-4-carboxylic acid (pyridin-3-ylmethyl)-amide, 6-(3-Chloro-phenyl)-pyrimidine-4-carboxylic acid pyridazin-3-ylamide, 6-(3-Chloro-phenyl)-pyrimidine-4-carboxylic acid pyrazin-2-ylamide, 6-(3,4-Dichloro-phenyl)-pyrimidine-4-carboxylic acid (5-methoxy-pyridin-3-yl)-amide, 6-(3,4-Dichloro-phenyl)-pyrimidine-4-carboxylic acid pyrimidin-5-ylamide, 6-(3,4-Dichloro-phenyl)-pyrimidine-4-carboxylic acid (6-methyl-pyridin-3-yl)-amide, 6-(3,4-Dichloro-phenyl)-pyrimidine-4-carboxylic acid (2-methyl-pyridin-3-yl)-amide, 6-(3-Chloro-phenyl)-pyrimidine-4-carboxylic acid pyrimidin-2-ylamide, 6-(3-Chloro-phenyl)-pyrimidine-4-carboxylic acid (6-methyl-pyridin-3-yl)-amide, 6-(3-Chloro-phenyl)-pyrimidine-4-carboxylic acid (2-methyl-pyridin-3-yl)-amide, 6-(3,5-Dichloro-phenyl)-pyrimidine-4-carboxylic acid (5-methoxy-pyridin-3-yl)-amide, 6-(3-Chloro-phenyl)-pyrimidine-4-carboxylic acid (1-methyl-1H-pyrazol-3-yl)-amide, 6-(3-Chloro-phenyl)-pyrimidine-4-carboxylic acid (1-methyl-1H-pyrazol-4-yl)-amide, 6-(3-Fluoro-phenyl)-pyrimidine-4-carboxylic acid pyridin-3-ylamide, 6-(3,5-Dichloro-phenyl)-pyrimidine-4-carboxylic acid pyrimidin-5-ylamide, 6-(3-Chloro-4-trifluoromethyl-phenyl)-pyrimidine-4-carboxylic acid pyridin-3-ylamide, [6-(3-Chloro-phenyl)-pyrimidin-4-yl]-(2,3-dihydro-pyrrolo[3,2-c]pyridin-1-yl)-methanone, 6-(3-Chloro-phenyl)-pyrimidine-4-carboxylic acid thiazol-2-ylamide, 6-(3-Chloro-phenyl)-pyrimidine-4-carboxylic acid (3-methyl-isoxazol-5-yl)-amide, 6-(3-Chloro-phenyl)-pyrimidine-4-carboxylic acid (5-methyl-[1,3,4]oxadiazol-2-yl)-amide, 6-(3-Chloro-phenyl)-pyrimidine-4-carboxylic acid oxazol-2-ylamide, 6-(3-Chloro-phenyl)-pyrimidine-4-carboxylic acid (3-methyl-[1,2,4]thiadiazol-5-yl)-amide, 6-(3-Chloro-phenyl)-pyrimidine-4-carboxylic acid (4H-[1,2,4]triazol-3-yl)-amide, 6-(3,4-Difluoro-phenyl)-pyrimidine-4-carboxylic acid pyrimidin-5-ylamide, 6-(3,4-Dichloro-phenyl)-pyrimidine-4-carboxylic acid (2,6-dimethyl-pyridin-3-yl)-amide, 6-(3,4-Dichloro-phenyl)-pyrimidine-4-carboxylic acid (3-methyl-isoxazol-5-yl)-amide, 6-(3,4-Dichloro-phenyl)-pyrimidine-4-carboxylic acid (5-methyl-[1,3,4]oxadiazol-2-yl)-amide, 6-(3,4-Dichloro-phenyl)-pyrimidine-4-carboxylic acid (pyridin-4-ylmethyl)-amide, 6-(3,4-Dichloro-phenyl)-pyrimidine-4-carboxylic acid [1,3,4]thiadiazol-2-ylamide, 6-(3,4-Dichloro-phenyl)-pyrimidine-4-carboxylic acid pyridin-4-ylamide, 6-(3,4-Dichloro-phenyl)-pyrimidine-4-carboxylic acid pyridin-2-ylamide, 6-(3,4-Dichloro-phenyl)-pyrimidine-4-carboxylic acid (1-methyl-1H-pyrazol-4-yl)-amide, 6-(3,4-Dichloro-phenyl)-pyrimidine-4-carboxylic acid isoxazol-3-ylamide, 6-(3,4-Dichloro-phenyl)-pyrimidine-4-carboxylic acid thiazol-2-ylamide, 6-(3,4-Dichloro-phenyl)-pyrimidine-4-carboxylic acid (4H-[1,2,4]triazol-3-yl)-amide, 6-(3,4-Difluoro-phenyl)-pyrimidine-4-carboxylic acid pyridin-3-ylamide, 6-(3-Trifluoromethyl-phenyl)-pyrimidine-4-carboxylic acid pyrimidin-5-ylamide, 6-(3,4-Dichloro-phenyl)-pyrimidine-4-carboxylic acid (2-methyl-pyrimidin-5-yl)-amide, 6-(3-Chloro-4-fluoro-phenyl)-pyrimidine-4-carboxylic acid pyridin-3-ylamide, 6-(3-Chloro-4-fluoro-phenyl)-pyrimidine-4-carboxylic acid (2,6-dimethyl-pyridin-3-yl)-amide, 6-(3-Chloro-4-fluoro-phenyl)-pyrimidine-4-carboxylic acid pyrimidin-5-ylamide, 6-(3,4-Dichloro-phenyl)-5-fluoro-pyrimidine-4-carboxylic acid pyridin-3-ylamide, 6-(3,4-Dichloro-phenyl)-5-fluoro-pyrimidine-4-carboxylic acid pyridin-3-ylamide, 6-(3,4-Dichloro-phenyl)-5-fluoro-pyrimidine-4-carboxylic acid (2,6-dimethyl-pyridin-3-yl)-amide, 6-(3,4-Dichloro-phenyl)-5-fluoro-pyrimidine-4-carboxylic acid pyrimidin-5-ylamide, 6-(3-Chloro-phenyl)-pyrimidine-4-carboxylic acid (3,5-dimethyl-isoxazol-4-yl)-amide, 6-(5-Chloro-2-fluoro-phenyl)-pyrimidine-4-carboxylic acid pyridin-3-yl-amide, 6-(3,4-Dichloro-phenyl)-pyrimidine-4-carboxylic acid oxazol-2-yl-amide, 6-(3,4-Dichloro-phenyl)-pyrimidine-4-carboxylic acid (3-methyl-[1,2,4]-thiadiazol-5-yl)-amide, 6-(4-Chloro-3-fluoro-phenyl)-pyrimidine-4-carboxylic acid pyridin-3-yl-amide, 6-(4-Chloro-3-fluoro-phenyl)-pyrimidine-4-carboxylic acid (2,6-dimethyl-pyridin-3-yl)-amide, 6-(3,4-Dichloro-phenyl)-pyrimidine-4-carboxylic acid ((R)-1-phenyl-ethyl)-amide, 6-(3,4-Dichloro-phenyl)-pyrimidine-4-carboxylic acid (tetrahydro-pyran-4-ylmethyl)-amide, 6-(3,4-Dichloro-phenyl)-pyrimidine-4-carboxylic acid (tetrahydro-pyran-4-yl)-amide, 6-(3,4-Dichloro-phenyl)-pyrimidine-4-carboxylic acid (5-methyl-[1,3,4]oxadiazol-2-ylmethyl)-amide, 6-(3,4-Dichloro-phenyl)-pyrimidine-4-carboxylic acid (1-methyl-1H-pyrazol-3-yl)-amide, 6-(3,4-Dichloro-phenyl)-pyrimidine-4-carboxylic acid pyridazin-3-yl-amide, 6-(3,4-Dichloro-phenyl)-pyrimidine-4-carboxylic acid pyrazin-2-yl-amide, 6-(3,4-Dichloro-phenyl)-pyrimidine-4-carboxylic acid (5-tert-butyl-[1,3,4]oxadiazol-2-yl)-amide, 6-(4-Chloro-phenyl)-pyrimidine-4-carboxylic acid pyridin-3-yl-amide, 6-(4-Chloro-phenyl)-pyrimidine-4-carboxylic acid pyrimidin-5-ylamide, 6-(3,4-Dichloro-phenyl)-pyrimidine-4-carboxylic acid ((S)-1-pyridin-4-yl-ethyl)-amide, 6-(3,4-Dichloro-phenyl)-pyrimidine-4-carboxylic acid ((R)-1-pyridin-3-yl-ethyl)-amide, 6-(3-Chloro-phenyl)-pyrimidine-4-carboxylic acid ((S)-1-pyridin-4-yl-ethyl)-amide, 6-(3,4-Dichloro-phenyl)-pyrimidine-4-carboxylic acid ((S)-1-pyridin-3-yl-ethyl)-amide, 6-(4-Chloro-2-fluoro-phenyl)-pyrimidine-4-carboxylic acid pyridin-3-yl-amide, 6-(3,4-Dichloro-phenyl)-pyrimidine-4-carboxylic acid (1-methyl-1H-indazol-3-yl)-amide, 6-(3-Fluoro-phenyl)-pyrimidine-4-carboxylic acid pyrimidin-5-yl-amide, 6-(4-Chloro-2-fluoro-phenyl)-pyrimidine-4-carboxylic acid pyrimidin-5-yl-amide, 6-(3,4-Dichloro-phenyl)-pyrimidine-4-carboxylic acid (2,2,6,6-tetramethyl-piperidin-4-yl)-amide, 6-(3,4-Dichloro-phenyl)-pyrimidine-4-carboxylic acid (2,2,6,6-tetramethyl-piperidin-4-yl)-amide hydrochloride salt, 6-(3,4-Dichloro-phenyl)-pyrimidine-4-carboxylic acid [1-(3-oxo-3,4-dihydro-2H-benzo[1,4]oxazin-6-yl)-ethyl]-amide, 6-(3,4-Dichloro-phenyl)-pyrimidine-4-carboxylic acid (tetrahydro-furan-3 S-yl)-amide, 6-(3,4-Dichloro-phenyl)-pyrimidine-4-carboxylic acid (tetrahydro-furan-3R-yl)-amide, 6-(3,4-Dichloro-phenyl)-pyrimidine-4-carboxylic acid (1-piperidin-4-yl-ethyl)-amide hydrochloride salt, 6-(3-Chloro-2-fluoro-phenyl)-pyrimidine-4-carboxylic acid pyridin-3-yl-amide, 6-(3,4-Dichloro-phenyl)-pyrimidine-4-carboxylic acid (4-dimethylamino-tetrahydro-pyran-4-ylmethyl)-amide hydrochloride salt, 6-(3,4-Dichloro-phenyl)-pyrimidine-4-carboxylic acid (2,4-dimethyl-pyridin-3-yl)-amide, 6-(3,4-Dichloro-phenyl)-pyrimidine-4-carboxylic acid (6-methyl-pyridazin-3-yl)-amide, 6-(3,4-Dichloro-phenyl)-pyrimidine-4-carboxylic acid (1-azabicyclo[2.2.2]oct-3-yl)-amide, 6-(3,4-Dichloro-phenyl)-pyrimidine-4-carboxylic acid (3-tert-butyl-isothiazol-5-yl)-amide, 6-(3,4-Dichloro-phenyl)-pyrimidine-4-carboxylic acid (3,5-dimethyl-pyrazin-2-yl)-amide, 6-(3,4-Dichloro-phenyl)-pyrimidine-4-carboxylic acid [1,3,4]oxadiazol-2-ylamide, 6-(3,4-Dichloro-phenyl)-pyrimidine-4-(1-aza-bicyclo[2.2.2]oct-4-ylmethyl)-amide hydrochloride salt, 6-(3,4-Dichloro-phenyl)-pyrimidine-4-carboxylic (3-trifluoromethyl-isoxazol-5-yl)-amide, 6-(3,4-Dichlorophenyl)-pyrimidine-4-carboxylic acid (5-oxo-pyrrolidin-3-yl)-amide, 6-(3,4-Dichloro-phenyl)-pyrimidine-4-carboxylic acid [5-(1-hydroxy-1-methyl-ethyl)-[1,3,4]oxadiazol-2-yl]-amide, 6-(3,4-Dichloro-phenyl)-pyrimidine-4-carboxylic acid (5-oxo-pyrrolidin-2-yl)-amide, 6-(3,4-Dichloro-phenyl)-pyrimidine-4-carboxylic acid (5-trifluoromethyl-[1,3,4]oxadiazol-2-yl)-amide, 6-(3-Bromo-phenyl)-pyrimidine-4-carboxylic acid (5-methyl-[1,3,4]oxadiazol-2-yl)-amide, 6-(3,4-Dichloro-phenyl)-pyrimidine-4-carboxylic acid (4-hydroxy-tetrahydro-pyran-4-ylmethyl)-amide, 6-(3,4-Dichloro-phenyl)-pyrimidine-4-carboxylic acid (S)-pyrrolidin-3-ylamide hydrochloride salt, or 6-(3,4-Dichloro-phenyl)-pyrimidine-4-carboxylic acid (R)-pyrrolidin-3-ylamide hydrochloride salt.

In some embodiments, the compound is not 6-(3,4-Dichloro-phenyl)-pyrimidine-4-carboxylic acid (5-oxo-pyrrolidin-2-yl)-amide.

In some embodiments, $X^1$ is not 3,4-dichlorophenyl.

In some embodiments, the compound of Formula I is labeled with one or more radioactive isotopes. In some embodiments, the compound of Formula I contains one or more positron-emitting radioactive isotopes selected from $^{11}C$, $^{13}N$, $^{15}O$, and $^{18}F$.

In some embodiments, an imaging agent comprising the compound of Formula I, or an isotopically enriched analog, pharmaceutically acceptable salt, prodrug, tautomer, stereoisomer, or a mixture of stereoisomers thereof, is provided.

Also provided are additional compounds as described herein. In some embodiments, provided is a compound selected from Table 1, or an isotopically labeled analog, pharmaceutically acceptable salt, solvate, prodrug, stereoisomer, or mixture of stereoisomers thereof.

In some embodiments, provided is a pharmaceutical composition comprising the compound described herein, or an isotopically enriched analog, pharmaceutically acceptable salt, prodrug, tautomer, stereoisomer, or a mixture of stereoisomers thereof, and a pharmaceutically acceptable excipient.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

In some embodiments, provided is a compound selected from those described in the Examples section provided herein.

Also is provided a compound, or an isotopically enriched analog, pharmaceutically acceptable salt, prodrug, tautomer, stereoisomer, or a mixture of stereoisomers thereof, selected from Table 1:

TABLE 1

| Ex | Structure |
|---|---|
| 1 | |
| 2 | 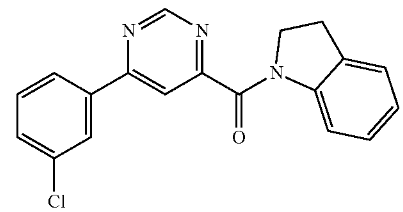 [SMILES: O=C(c1cc(-c2cccc(Cl)c2)ncn1)N1CCc2ccccc21] |
| 3 | 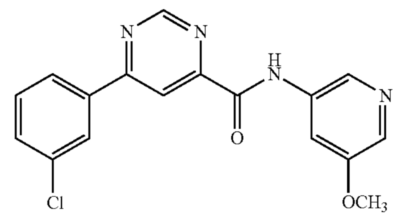 [SMILES: COc1cncc(NC(=O)c2cc(-c3cccc(Cl)c3)ncn2)c1] |
| 4 | 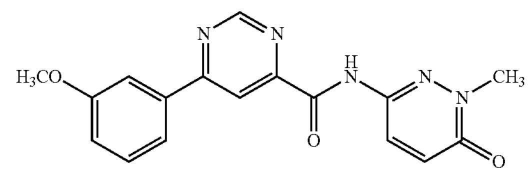 |
| 5 | 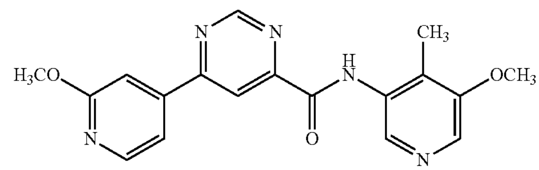 [SMILES: COc1cc(-c2cc(C(=O)Nc3cncc(OC)c3C)ncn2)ccn1] |
| 6 | 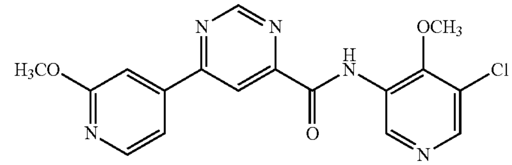 [SMILES: COc1cc(-c2cc(C(=O)Nc3cncc(Cl)c3OC)ncn2)ccn1] |
| 7 | 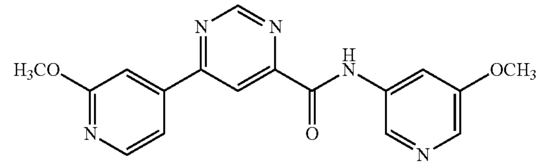 [SMILES: COc1cncc(NC(=O)c2cc(-c3ccnc(OC)c3)ncn2)c1] |
| 8 | 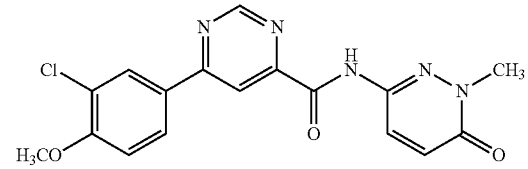 [SMILES: COc1ccc(-c2cc(C(=O)Nc3ccc(=O)n(C)n3)ncn2)cc1Cl] |
| 9 | 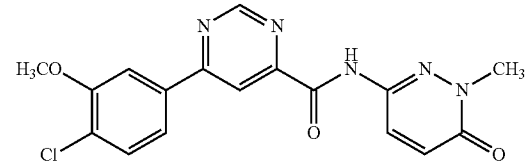 |

TABLE 1-continued

| Ex | Structure |
|----|-----------|
| 10 | 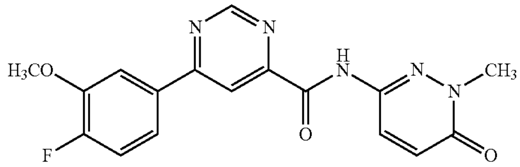 [SMILES: COc1cc(-c2cc(C(=O)Nc3ccc(=O)n(C)n3)ncn2)ccc1F] |
| 11 | 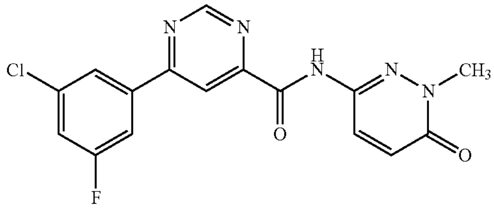 [SMILES: Cn1nc(NC(=O)c2cc(-c3cc(F)cc(Cl)c3)ncn2)ccc1=O] |
| 12 | 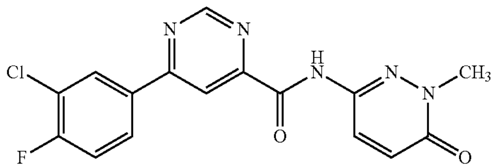 [SMILES: Cn1nc(NC(=O)c2cc(-c3ccc(F)c(Cl)c3)ncn2)ccc1=O] |
| 13 | 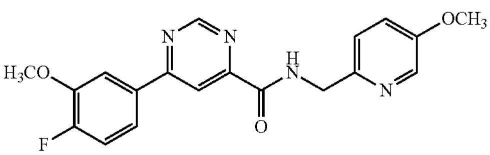 [SMILES: COc1ccc(CNC(=O)c2cc(-c3ccc(F)c(OC)c3)ncn2)nc1] |
| 14 | 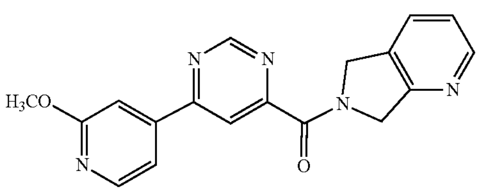 [SMILES: COc1cc(-c2cc(C(=O)N3Cc4cccnc4C3)ncn2)ccn1] |
| 15 | 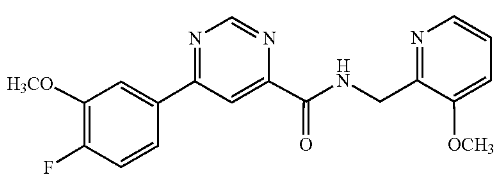 [SMILES: COc1cc(-c2cc(C(=O)NCc3ncccc3OC)ncn2)ccc1F] |
| 16 | 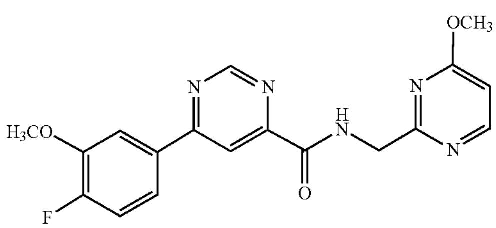 [SMILES: COc1ccnc(CNC(=O)c2cc(-c3ccc(F)c(OC)c3)ncn2)n1] |
| 17 | 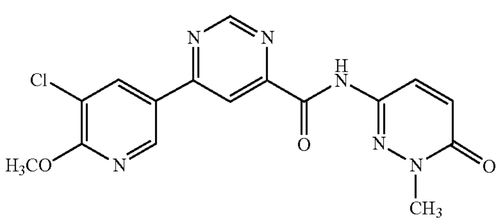 [SMILES: COc1ncc(-c2cc(C(=O)Nc3ccc(=O)n(C)n3)ncn2)cc1Cl] |
| 18 | |
| 19 | |
| 20 | |
| 21 | |
| 22 | |
| 23 | |
| 24 | |

TABLE 1-continued

| Ex | Structure |
|---|---|
| 25 | (structure) |
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |
| 37 | (structure) |
| 38 | (structure) |

TABLE 1-continued

| Ex | Structure |
|---|---|
| 39 | 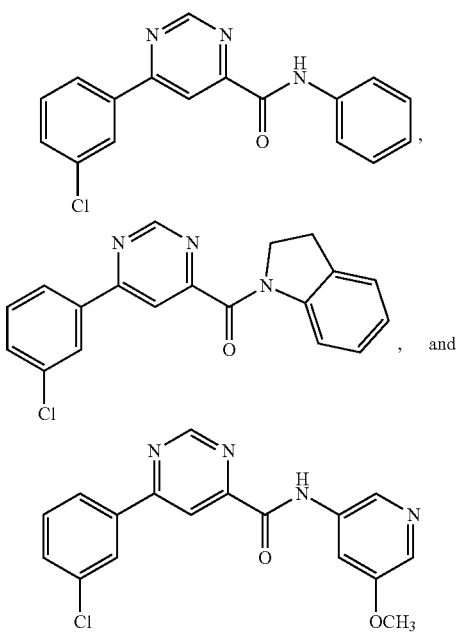 |
| 40 | 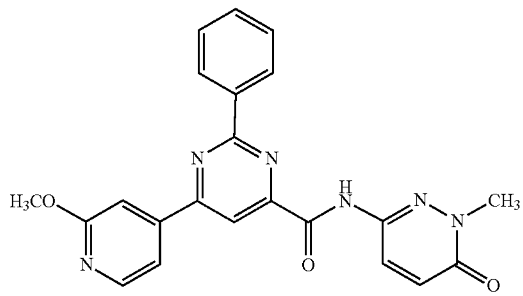 [SMILES: COc1cc(-c2cc(C(=O)Nc3ccc(=O)n(C)n3)nc(-c3ccccc3)n2)ccn1] |
| 41 | | wherein the compound is optionally labeled with one or more radioactive isotopes, except that are labeled with one or more radioactive isotopes.

Diagnostic Methods and Uses

In some embodiments, a method of generating diagnostic images in an individual is provided, comprising administering an effective amount of a compound or an imaging agent described herein to an individual, and generating an image of a body part or body area of the individual. Generating an image of a body part or body area of the individual may comprise generating an image to detect the presence or absence of a protein susceptible to aggregation in the image. Thus, the compounds disclosed herein are useful for detecting a disease or condition mediated, at least in part, by a protein susceptible to protein aggregation. In some embodiments, the presence or absence of a protein aggregate corresponds to the presence or absence of a neurodegenerative disease. In some embodiments, the neurodegenerative disease is selected from Alzheimer's disease, amyotrophic lateral sclerosis, Huntington's disease, Parkinson's disease, Prion disease and spinocerebellar ataxias.

Provided are methods of generating diagnostic images using positron emission tomography (PET). PET imaging may be conducted as known to those of skill in the art, or as follows. PET imaging may involve the administration of a positron-emitting radionuclide tracer, for example, a compound or imaging agent described herein, to an individual. The tracer is then given sufficient time to associate with the protein of interest, at which time the individual is placed in a scanning device comprising a ring of scintillation detectors. An emitted positron travels through the individual's tissue for a short (isotope-dependent) distance, until it interacts with an electron. The interaction annihilates both the electron and the positron, producing a pair of photons. The photons are detected by a scintillator in the scanning device. Photons that do not arrive in pairs are ignored.

Also provided are methods of generating diagnostic images comprising PET with concurrent computed tomography imaging (PET/CT), with concurrent magnetic resonance imaging (PET/MRI), or single-photon emission computed tomography (SPECT) imaging. In general, computed tomography uses X-rays or gamma rays to detect the structure of the brain, while magnetic resonance imaging uses magnetic fields and radio waves.

Thus, a compound or an imaging agent described herein may be administered by methods known in the art including those described herein. The compound or imaging agent may enter circulation and bind to the protein susceptible to aggregation, or to aggregates thereof. When the compound or imaging agent is labeled with a radioactive isotope, the emitted particles may be detected.

In some embodiments the compound or imaging agent is administered into the individual's vascular system. The compound or imaging agent may pass through the blood-brain barrier. Thus, generating an image may comprise generating an image of at least part of the individual's brain, for example, the part to which the compound has distributed.

Also provided are methods of generating diagnostic images in a biological sample comprising contacting the biological sample with an effective amount of a compound or an imaging agent described herein and generating an image associated with the biological sample. In some embodiments, the contacting and the generating may be conducted in vitro. In some embodiments the contacting is in vivo and the generating is in vitro.

Also provided are methods for detecting the presence or absence of a pathologic process associated with a protein susceptible to protein aggregation, for example huntingtin protein (HTT protein), in an individual comprising: administering an effective amount of a compound or an imaging agent described herein; generating an image to detect the presence or absence of huntingtin protein (HTT protein) in the image; and detecting the presence or absence of a pathologic process, e.g., a neurodegenerative disease. In some embodiments, the HTT protein is present as monomers, oligomers, or aggregates, or a combination thereof. In some embodiments, the protein susceptible to aggregation is huntingtin protein (HTT protein). The HTT protein may be mutant. In some embodiments, the HTT protein is found in the brain, for example, in basal ganglia.

In some embodiments, the body part or body area is selected from head, spinal cord, limb, thorax, and/or abdomen. In some embodiments, the body part or body area is a brain. In some embodiments, the HTT protein is found in basal ganglia. In some embodiments, the protein susceptible to aggregation, e.g., HTT protein, is present in the brain, liver, heart, and/or muscle of the individual. In some embodiments, generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof. In some embodiments, generating an image comprises PET imaging. In some embodiments, the protein susceptible to aggregation, e.g., HTT protein, is present in the basal ganglia, cortex, hippocampus, and/or brain stem of the brain of the individual. In some embodiments, the protein susceptible to aggregation, e.g., HTT protein, is present as monomers, oligomers, or aggregates, or a combination thereof.

In some embodiments, the individual has, or is discovered to have, Huntington's disease.

Also provided are methods for detecting the presence or absence of a pathologic process associated with β-amyloid protein in an individual comprising: administering an effective amount of a compound or an imaging agent described herein; generating an image of a body part or body area of the individual; and detecting the presence or absence of the pathologic process. In some embodiments, the individual has, or is discovered to have, Alzheimer's Disease (AD).

Also provided are diagnostic methods of using a compound or an imaging agent described herein to monitor disease progression in a patient by quantifying the change in levels of the protein susceptible to aggregation in the patient.

In some embodiments, provided is a compound having suitable protein aggregate, e.g., HTT protein aggregate or β-amyloid protein aggregate, binding kinetics to function as imaging agents. Thus, a compound described herein may be characterized by one or more of: 1) a high affinity for such protein aggregates; 2) a low affinity for nearby structures; and/or 3) slow dissociation kinetics from such protein aggregates. Dissociation kinetics may be expressed as the dissociation rate constant $k_{diss}$ as defined in the equation below (wherein A and B refer to the protein aggregate and the imaging agent, and $k_{assn}$ is the association rate constant):

$$d[AB]/dt = k_{assn}[A][B] - k_{diss}[AB]$$

In some embodiments, the effective amount of the compound or imaging agent described herein comprises from about 0.1 to about 20 mCi. In some embodiments, the effective amount of the compound or imaging agent described herein comprises about 0.1, about 0.3, about 0.5, about 0.7, about 1, about 3, about 5, about 7, about 10, about 15, or about 20 mCi, or a range of values therebetween. In some embodiments, the effective amount of the compound or imaging agent described herein comprises about 10 mCi.

Suitable radionuclides that may be incorporated in a compound described herein include, but are not limited to, $^{3}H$ (also written as T), $^{11}C$, $^{18}F$, $^{35}$, $^{123}I$, $^{125}I$, $^{75}Br$, $^{76}Br$, $^{77}Br$, $^{82}Br$, $^{131}I$, $^{15}O$, $^{13}N$, and $^{211}At$. The radionuclide that is incorporated in the compound will depend on the specific imaging application. In some embodiments including PET imaging, compounds that incorporate a radionuclide selected from $^{11}C$, $^{18}F$, $^{123}I$, $^{131}I$, $^{75}Br$, $^{76}Br$ or $^{77}Br$ may be used. In certain applications incorporation of a chelating radionuclide such as $^{99m}Tc$ may also be useful. In some embodiments, $^{18}F$ may be preferable over $^{11}C$ because with the longer half-life of $^{18}F$, imaging can be carried out long enough to allow a stronger signal to develop. In some embodiments, a compound or imaging agent described herein can be labeled with a positron emitting radionuclide or a gamma emitting radionuclide. Some examples of positron-emitting radionuclides include $^{15}O$, $^{13}N$, $^{11}C$, $^{18}F$, $^{76}Br$, and $^{124}I$, which have half-lives of about 2, 10, 20, 110 minutes, 16 hours, and 4.2 days respectively.

In some embodiments, a compound or an imaging agent described herein may be labelled with a positron emitter selected from $^{11}C$ and $^{18}F$. Methods for the introduction of $^{11}C$ may include, but are not limited to, alkylation with [$^{11}C$]iodomethane or [$^{11}C$]methyl triflate. Carbon-11 has a half-life of approximately 20 minutes, thus $^{11}C$ generally needs to be generated in an on-site cyclotron, and may be produced as [$^{11}C$]carbon dioxide. The [$^{11}C$]carbon dioxide is converted to the chemical species appropriate for the radiosynthesis (generally [$^{11}C$]iodomethane or the like), and the synthesis of the radiopharmaceutical is completed and used on-site in a PET imaging study after the appropriate radiochemical purity and specific activity have been determined. Typical methods of introducing $^{18}F$ include but are not limited to nucleophilic and electrophilic methods. Nucleophilic methods include displacement of a halide, tosylate, or other leaving group with labeled cesium fluoride, potassium fluoride, tetrabutylammonium fluoride, tetramethylammonium fluoride, or potassium fluoride kryptofix-222. Electrophilic reagents that may be suitable for introducing [$^{18}F$] isotopes include labeled diethylaminosulfur trifluoride (DAST), bis(2-methoxyethyl)aminosulfur trifluoride (Deoxofluor), N-fluorobenzenesulfonimide (NFSI), N-fluoropyridinium salts, 1-chloromethyl-4-fluoro-1,4-diazoniabicyclo[2.2.2]octane bis(tetrafluoroborate) (Selectfluor), N-fluoropyridinium triflate, xenon fluoride, 2-pyridinesulfonyl fluoride (PyFluor), 3-pyridinesulfonyl fluoride, 4-pyridinesulfonyl fluoride, 4-chloro-2-pyridinesulfonyl fluoride, ethenesulfonyl fluoride, fluoro-benziodoxole, p-fluorophenylaminosulfur trifluoride, p-nitrophenylaminosulfur trifluoride, or pentafluorophenylaminosulfur trifluoride. General methods for the introduction of positron emitters are described in the literature (e.g., see Miller et al., *Angewandte Chemie International Edition*, 47 (2008), 8998-9033; Jacobson, O. et al., Bioconjugate Chem., 26 (2015), 1-18; Deng, X. et al., *Angewandte Chemie International Edition*, 58(9), (2019), 2580-2605).

Fluorine-18 has a half-life of approximately 110 minutes, thus synthesis of [$^{18}F$]radiopharmaceuticals need not necessarily have to occur at the site of the cyclotron nor proximal to the PET imaging study center. Fluorine-18 is also thought to exhibit favorable nuclear and physical characteristics, including high positron decay ratio (97%), relatively short half-life (109.7 min), and low positron energy (up to 0.635 MeV). The positron energy may correspond to a short diffusion range (<2.4 mm) in vivo that may provide superior resolution limits of a PET image.

As will be recognized, the steps of the methods described herein need not be performed any particular number of times or in any particular sequence. Additional objects, advantages and novel features of the disclosure will become apparent to those skilled in the art upon examination of the examples provided below, which are intended to be illustrative and are not limiting.

Indications and Treatment Methods

A compound or an imaging agent described herein may be useful for treating a disease or condition mediated, at least in part, by a protein susceptible to aggregation. In some embodiments, a compound or an imaging agent described herein is useful for treating a disease or condition mediated, at least in part, by HTT protein. In some embodiments, treatment of a disease or condition mediated, at least in part, by a protein susceptible to aggregation may comprise administration of a compound or an imaging agent described herein. Treatment may include coadministration of a compound or an imaging agent described herein and one or more other active agents and/or therapies. Thus, in some embodiments, provided is a method of treating or preventing a disease or condition mediated, at least in part, by a protein susceptible to aggregation in a patient in need thereof, comprising administering to the patient a therapeutically effective amount of a compound or an imaging agent described herein.

Exemplary diseases and conditions are as follows.

Huntington's Disease (HD)

Huntington's disease (HD) is an inherited progressive neurodegenerative disorder, characterized by motor, cognitive, and psychiatric deficits as well as neurodegeneration and brain atrophy. Atrophy may begin in the striatum and cortex and extend to other subcortical brain regions. HD belongs to a family of neurodegenerative diseases in which an expanded CAG repeat tract results in long stretches of polyglutamine (polyQ) in an encoded protein. The family also includes dentatorubral-pallidoluysian atrophy (DR-PLA), spinal and bulbar muscular atrophy (SBMA) and the spinocerebellar ataxias (SCAs). In HD, the selective neurodegeneration of the γ-aminobutyric acid-releasing spiny-projection neurons of the striatum had been observed, although neuron loss in many other brain regions has also been reported. Symptoms of HD include loss of motor control, psychiatric symptoms, memory and/or cognitive impairment.

HD protein huntingtin (HTT protein) is a 348-kDa multidomain protein that contains a polymorphic glutamine/proline-rich domain at its amino-terminus. The number of CAG repeats in the $IT_{15}$ gene varies from 6 to 35 in healthy individuals; repeats of 36 or more define an HD allele. The length of the CAG expansion has been inversely correlated with age of disease onset, with cases of juvenile onset characterized by expansions of more than 60 repeats. The longer polyQ domain is believed to induce conformational changes in the HTT protein, which causes it to form intracellular aggregates that, in many, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

The part of the brain most affected by HD, and thus believed to be most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

Basal ganglia are a group of subcortical nuclei responsible primarily for motor control, as well as other roles such as motor learning, executive functions and behaviors, and emotions. Disruption of the basal ganglia network are believed to contribute to several movement disorders. Normal function of the basal ganglia requires fine tuning of neuronal excitability within each nucleus to determine the degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

The administration of a compound described herein may result in a decrease, for example, at least a 10% decrease (e.g., at least 15%, 20%, 25%, 30%, 35%, 40%, 45%, 50%, 55%, 60%, 65%, 70%, 75%, 80%, 85%, 90% or 100%) in one or more symptoms of a disease or condition described herein. The disease or condition may be a disorder of the nervous system that is secondary to a disease, condition, or therapy having a primary effect outside of the nervous system; an injury to the nervous system caused by physical, mechanical or chemical trauma; autoimmune neural degeneration; neurodegeneration secondary to infection; and/or ocular neurodegeneration. Symptoms of nerve degeneration include, e.g., tremors, slowness of movement, ataxia, loss of balance, depression, decreased cognitive function, short term memory loss, long term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

A neurodegenerative disease is a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion disease, Refsum's disease, Sandhoff disease, Schilder's disease, Subacute combined degeneration of spinal cord secondary to Pernicious Anaemia, Schizophrenia, Spinocerebellar ataxia, Spinal muscular atrophy, Steele-Richardson-Olszewski disease, insulin resistance or Tabes dorsalis.

In some embodiments, the disease or condition is selected from Huntington's disease (HD), dentatorubro-pallidoluysian atrophy, spinal and bulbar muscular atrophy, spinocerebellar ataxia, spinal cord and/or brain injury, chronic pulmonary hypertension, Parkinson's disease, amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma.

A compound described herein, when administered to a subject, may inhibit neuron degeneration. In some embodiments, inhibiting neuron degeneration may include inhibiting axon or neuron degeneration in a neuron. Such inhibition with respect to the entire neuron or a portion thereof, such as the neuron cell body, axons and dendrites. This can be assessed, for example, by analysis of neurological function according to methods known in the art. The administration of a compound described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or 100%) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the compounds described herein.

Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the disclosure include cerebellar granule neurons, dorsal root ganglion neurons, PNS neurons (e.g. sensory neurons), and cortical neurons. Other examples of cell types that may be subject to treatment according to the disclosure include astrocytes and microglia.

Further, the compounds described herein can be used in the prevention or treatment of memory loss. Types of memory that can be affected by loss, and thus treated according to the disclosure, include episodic memory, semantic memory, short-term memory, and long-term memory.

In some embodiments, the disease or condition is a neurodegenerative disease selected from Alzheimer's disease, amyotrophic lateral sclerosis, Huntington's disease, Parkinson's disease, Prion disease and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the pathologic process is associated with, or caused by, a disease or condition selected from Huntington's disease (HD), dentatorubro-pallidoluysian atrophy, spinal and bulbar muscular atrophy, spinocerebellar ataxia, spinal cord and/or brain injury, chronic pulmonary hypertension, Parkinson's disease, Amyotrophic lateral sclerosis, cerebral cavernous malformation, cardiovascular disease, Alzheimer's disease (AD), glaucoma, multiple sclerosis (MS), corneal lesions, diabetes, chronic and/or neuropathic pain, stroke, ischemia, retinopathy, spinal muscular atrophy (SMA), erectile dysfunction, nephropathy (non-hypertensive), hypertensive nephropathy, hypertension (high blood pressure), optic nerve lesion, hepatic fibrosis, lupus, liver failure after transplant, encephalomyelitis, epilepsy, and glioblastoma. In some embodiments, the pathologic process is a neurodegenerative disease selected from Alzheimer's disease, amyotrophic lateral sclerosis, Huntington's disease, Parkinson's disease, Prion disease and spinocerebellar ataxias. In some embodiments, the neurodegenerative disease is classified as a trinucleotide repeat disorder. In some embodiments, the trinucleotide repeat disorder is classified as belonging to Category I, Category II, or Category III.

In some embodiments, the neurodegenerative disease is Huntington's disease.

Also provided is use of a compound described herein for the manufacture of a medicament for use in diagnosis, prevention, or treatment of a disease or condition described herein. For example, the disease or condition may be Huntington's disease.

Imaging Agents and Pharmaceutical Compositions

An imaging agent will generally comprise a compound described herein labeled with a positron emitting radionuclide. Imaging agents labeled with positron emitting radionuclides are generally administered via intravenous injection shortly after synthesis (for example, within one hour) due to the short half-life of the radionuclides. The amount of imaging agent required will normally be determined by the prescribing physician. The dose may vary according to various factors, including but not limited to the associative kinetics of the compound, the quantity of emission from the radionuclide used, the half-life of the radionuclide, the body part, body area, and/or tissue to be imaged, and the characteristics of the individual. Those of ordinary skill in the art will appreciate that an effective amount will generally be the amount of labeled compound sufficient to produce emissions in the range of from about 0.1 to about 20 mCi, or about 1 to about 5 mCi. The mass of labeled compound in an effective amount of imaging agent may be about 0.1 to about 500 mg.

Generally, a compound or an imaging agent described herein may be administered to a patient in need thereof via any suitable route. Routes of administration may include, for example, parenteral administration, including subcutaneous, intramuscular, intravenous, by means of, for example a drip patch. Further suitable routes of administration include, but are not limited to, oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

With regard to PET imaging, administration of a compound or an imaging agent described herein to the individual may be intravenous. The pharmaceutical composition may be in the form of a sterile injectable aqueous or oleaginous suspension. This suspension may be formulated according to the known art using those suitable dispersing or wetting agents and suspending agents that have been mentioned herein. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables. Such solutions may be formulated as 0.01%-10% isotonic solutions, pH 5-7, with appropriate salts.

The compound or imaging agent described herein may be administered parenterally in a sterile medium. Parenteral administration includes subcutaneous injections, intravenous, intramuscular, intrathecal injection or infusion techniques. The compound or imaging agent described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

A pharmaceutical composition, for example, for injection, may comprise a cyclodextrin. The cyclodextrin may be, for example, a hydroxypropyl cyclodextrin or a sulfobutylether cyclodextrin. The cyclodextrin may be, for example, an α-cyclodextrin, a β-cyclodextrin, or a γ-cyclodextrin.

A compound or an imaging agent described herein may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

In some embodiments, the compound or imaging agent described herein is administered as a pharmaceutical composition. Accordingly, provided are pharmaceutical compositions comprising at least one compound or imaging agent described herein, together with at least one pharmaceutically acceptable vehicle chosen from carriers, adjuvants, and excipients. A compound or imaging agent of the present disclosure can be formulated into a pharmaceutical composition using techniques known to those of skill in the art.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound or imaging agent may be sufficient to provide a practical quantity of material for administration per dose of the compound or imaging agent.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENs®; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound or imaging agent described herein.

Effective concentrations of at least one compound or imaging agent described herein are mixed with a suitable pharmaceutically acceptable vehicle. In instances in which the compound or imaging agent exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous buffer, for example, sodium bicarbonate.

Upon mixing or addition of a compound or imaging agent described herein, the resulting mixture may be a solution, suspension, emulsion or the like. The form of the resulting mixture depends upon a number of factors, including the intended mode of administration and the solubility of the compound or imaging agent in the chosen vehicle. The effective concentration sufficient for imaging or treatment may be empirically determined according to known methods in the art.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of the compound or imaging agent described herein. In some embodiments, oral pharmaceutical compositions contain at least 5% (weight %) of the compound or imaging agent. Some embodiments contain from 25% to 50% or from 5% to 75% of the compound or imaging agent.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound or imaging agent described herein can be incorporated into oral liquid preparations such as aqueous or oily suspensions, solutions, emulsions, syrups, or elixirs, for example. Furthermore, pharmaceutical compositions containing the compound or imaging agent described herein can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monooleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, Avicel® RC-591, tragacanth and sodium alginate; typical wetting agents include lecithin and polysorbate 80; and typical preservatives include methyl paraben and sodium benzoate.

Aqueous suspensions containing the compound or imaging agent in admixture with excipients suitable for the manufacture of aqueous suspensions are provided. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the compound or imaging agent in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of an oil-in-water emulsion. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

The pharmaceutical composition may also be coated by conventional methods, typically with pH or time-dependent coatings, such that the compound or imaging agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit® coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

The compound or imaging agent described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound or imaging agent described herein may be formulated for local or topical application, such as for topical application to the skin and mucous membranes, such as in the eye, in the form of gels, creams, and lotions and for application to the eye. Topical pharmaceutical compositions may be in any form including, for example, solutions, creams, ointments, gels, lotions, milks, cleansers, moisturizers, sprays, skin patches, and the like.

Topical pharmaceutical compositions comprising at least one compound, or an isotopically labeled analog, pharmaceutically acceptable salt, solvate, prodrug, stereoisomer, or mixture of stereoisomers thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

The compound or imaging agent described herein may also be formulated for transdermal administration as a transdermal patch.

The compound or imaging agent described herein may also be administered in a liposome delivery system. Liposomes may be classified as small unilamellar vesicles, large unilamellar vesicles, and multilamellar vesicles. Liposomes can be formed from a variety of amphiphathic molecules, in particular phospholipids. Constituents of liposomes may include cholesterol, stearylamine and/or phosphatidylcholines. Liposomes are suitable for various routes of administration including topical and injection into various tissues. Thus, intravitreal (e.g., in treatment of glaucoma), intraperitoneal, intravenous, intravascular, intraarticular, and intramuscular administration of liposomes is contemplated.

Other pharmaceutical compositions useful for attaining systemic delivery of the compound or imaging agent include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound or imaging agent described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of the compound or imaging agent described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

The dose of the compound or imaging agent described herein depends upon a variety of factors including the particular pathologic process to be treated or detected, the physiology of the individual, the severity of the symptoms, the route of administration, the frequency of the dosage interval, the particular compound utilized, the efficacy, toxicology profile, pharmacokinetic profile of the compound, and the presence of any deleterious side-effects, among other considerations. The dose under a given set of circumstances generally will be determined by a practitioner on a case-by-case basis based on the above and other factors.

The compound or imaging agent described herein is typically administered at a dosage level and in a manner determined by a practitioner such as a physician. For example, the compound or imaging agent can be administered, in single or multiple doses, at a dosage level of generally 0.001-100 mg/kg, for example, 0.01-100 mg/kg, such as 0.1-70 mg/kg, for example, 0.5-10 mg/kg. The dose can be, for example, for administration once a day or twice a day. Unit dosage forms can contain generally 0.01-1000 mg of the compound or imaging agent described herein, for example, 0.1-50 mg. For intravenous administration, the compound or imaging agent can be administered, in single or multiple dosages, at a dosage level of, for example, 0.001-50 mg/kg, such as 0.001-10 mg/kg, for example, 0.01-1 mg/kg. Unit dosage forms can contain, for example, 0.1-10 mg of the compound or imaging agent.

Kits and Packaging

Also provided herein are kits that include a compound or imaging agent described herein and suitable packaging. In certain embodiments, a kit further includes instructions for use. In some embodiments, a kit includes a compound or an imaging agent described herein and a label and/or instructions for use of the compounds in the treatment of the indications, including the diseases or conditions, described herein.

Also provided herein are articles of manufacture that include a compound or an imaging agent described herein in a suitable container. The container may be a vial, jar, ampoule, preloaded syringe and intravenous bag.

Also provided are packaged pharmaceutical compositions. Such packaged compositions include a pharmaceutical composition comprising a compound or imaging agent described herein, and instructions for using the composition to treat a subject (typically a human patient). In some embodiments, the instructions are for using the pharmaceutical composition to detect a disease or condition described herein. The packaged pharmaceutical composition can include prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound or imaging agent can be administered alone, as mixtures, or in combination with other active agents.

Also provided is use of a compound or imaging agent described herein for the manufacture of a medicament for use in diagnosis, prevention, or treatment of a disease or condition described herein. For example, the disease or condition may be Huntington's disease.

Also provided is use of a compound described herein for the manufacture of an imaging agent for use in diagnosis, prevention, or treatment of a disease or condition described herein. For example, the disease or condition may be Huntington's disease.

Combination Therapy

The methods described herein include methods for detecting, treating or preventing a disease or condition described herein, comprising administering to a subject, simultaneously or sequentially, a compound or imaging agent described herein and one or more additional active agents. For example, the disease or condition may be Huntington's disease. In methods using simultaneous administration, the agents can be present in a combined composition or can be administered separately. When used in combination with one or more additional active agent or agents, a compound or imaging agent described herein may be administered prior to, concurrently with, or following administration of the additional active agent or agents. The administration can be by the same route or by different routes.

Also provided is a pharmaceutical composition comprising a compound or imaging agent described herein and one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. Similarly, also provided is a packaged pharmaceutical composition containing a pharmaceutical composition comprising a compound or imaging agent described herein, and another composition comprising one or more additional active agents used in the treatment of Huntington's disease such as, but not limited to, carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, and risperidone. In some embodiments, the active agent is carbamazepine, clonazepam, diazepam, fluoxetine, escitalopram, valproate, lamotrigine, amitriptyline, imipramine, desipramine, nortriptyline, paroxetine, fluoxetine, sertraline, tetrabenazine, haloperidol, chlorpromazine, thioridazine, sulpiride, quetiapine, clozapine, or risperidone.

Also provided are methods for treating or preventing Alzheimer's disease, including treating memory and/or cognitive impairment associated with Alzheimer's disease, comprising administering to a subject, simultaneously or sequentially, a compound or imaging agent described herein and one or more additional agents. In some embodiments, the active agent is Reminyl® (galantamine), Cognex® (tacrine), Aricept® (donepezil), Exelon® (rivastigmine), Akatinol® (memantine), Neotropin™ (somatropin), Eldepryl® (selegiline), Estrogen, or Clioquinol.

In some embodiments, compounds described herein can be administered with an active agent for treating Parkinson's disease, for example, with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In some embodiments, compounds described herein can be administered with an active agent for treating Alzheimer's disease, for example, with acetylcholinesterase inhibitors (e.g., donepezil, galantamine, and rivastigmine) and/or NMDA receptor antagonists (e.g., memantine).

Synthesis of the Compounds

A compound or imaging agent described herein may be prepared using the methods disclosed herein and routine modifications thereof, which will be apparent given the disclosure herein and methods well known in the art. Conventional and well-known synthetic methods may be used in addition to the teachings herein. The synthesis of a typical compound or imaging agent described herein may be accomplished as described in the following examples. If available, reagents may be purchased commercially, e.g., from Sigma Aldrich or other chemical suppliers.

A compound or imaging agent described herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006), Greene's protective groups in organic synthesis. Hoboken, N.J., Wiley-Interscience, and references cited therein.

Furthermore, a compound or imaging agent described herein may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromatography, chiral resolving agents, and the like. When enantiomerically pure or enriched compounds are desired, chiral chromatography and/or enantiomerically pure or enriched starting materials may be employed as conventionally used in the art or as described in the Examples.

The starting materials for the following reactions are generally known compounds or can be prepared by known procedures or obvious modifications thereof. For example, many of the starting materials are available from commercial suppliers such as Sigma Aldrich, Alfa Aesar, and the like. Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" and "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Generally, the term inert, as used herein with respect to a solvent, refers to a material that does not undergo reaction to form the target compound of interest through carbon-carbon bond forming reactions. Unless specified to the contrary, the solvents used in the reactions of the present disclosure are inert organic solvents, and the reactions are carried out under an inert gas, preferably nitrogen or argon.

The term "q.s." means adding a quantity sufficient to achieve a stated function, e.g., to bring a solution to the desired volume (i.e., 100%).

It will also be appreciated that in each of the below schemes, the addition of any substituent may result in the production of a number of isomeric products (including, but not limited to, enantiomers or one or more diastereomers) any or all of which may be isolated and purified using conventional techniques.

Incorporation of a label into a compound or imaging agent described herein may be conducted by reacting an appropriate starting material(s) with a reagent including a radioactive isotope. Methods typically follow the same principles as standard organic chemical reactions, and may be carried out by any method known to those of skill in the art, including those provided in the present disclosure.

Scheme 1 provides exemplary synthetic routes for the synthesis of compounds provided herein (e.g., compounds of Formula I).

In Scheme 1, Compound Va may be converted to Compound Vc by one or more steps. Compound Va may be reacted with Compound Vb to form Compound Vc. In Compound Va, $Z^1$ may be a suitable leaving group for a cross coupling reaction (e.g., a halo such as a chloro). $Z^2$ may be a suitable leaving group for an amide bond forming reaction (e.g., a hydroxyl or a halo such as a chloro, or a pseudohalide such as a sulfonyl). Where $Z^2$ is a hydroxyl, conditions for amide bond forming reaction between Compound Va and Compound Vb include a coupling agent for forming an amide bond (e.g., HATU, EDC), a base (e.g., triethylamine, diisopropylethylamine, pyridine), optionally a catalyst (e.g., 4-dimethylaminopyridine or hydroxybenzotriazole) and a suitable solvent (e.g., a polar aprotic solvent such as DMF or pyridine). Where $Z^2$ is a halide or a pseudohalide, conditions for amide bond forming reaction between Compound Va and Compound Vb include a base (e.g., NaH) and a suitable solvent (e.g., a polar aprotic solvent such as DMF) where Compound Vb may optionally be deprotonated before contacting with Compound Va.

Compound Vc may then be reacted with Compound Vd to form a compound of Formula I. In Compound Vd, $Z^3$ may be a suitable coupling partner (e.g., for metal-catalyzed cross coupling) for attaching $X^1$ (e.g., a boronic acid or boronic ester). Cross coupling may be accomplished in the presence of a catalyst (e.g., tetrakis(triphenylphosphine)palladium(0), dichloro[1,1'-bis(diphenylphosphino)ferrocene]palladium (II) dichloromethane adduct), optionally with a base (e.g., potassium carbonate, potassium phosphate), in a suitable solvent (e.g., 1,4-dioxane, DMF, acetonitrile/water), and optionally at an elevated temperature (e.g., 25 to 100° C.).

Alternatively, with reference to Scheme 1, Compound Ve may be reacted with Compound Vf to form Compound Vg under suitable conditions for cross coupling, for example, conditions described herein (e.g., with respect to reaction of

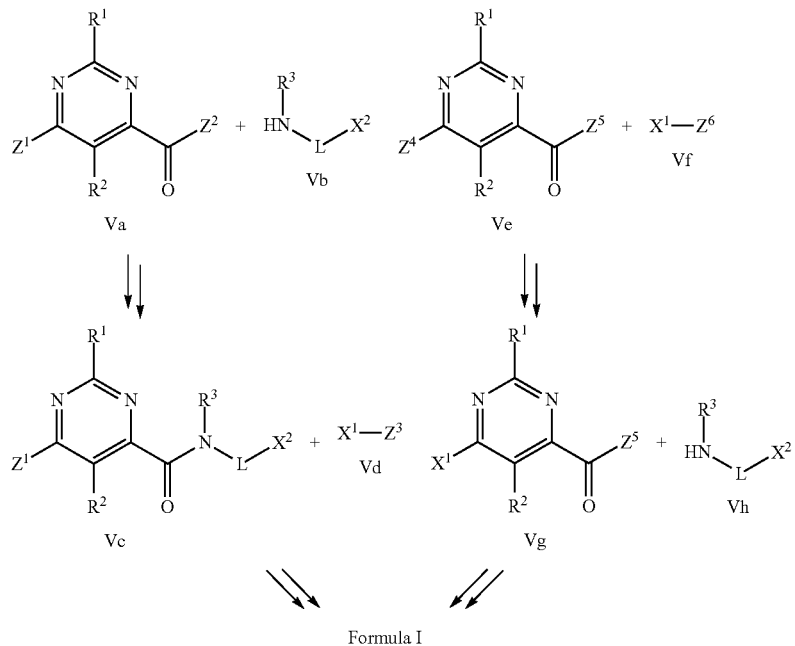

Scheme 1

In Scheme 1, $R^1$, $R^2$, $R^3$, L, $X^1$, and $X^2$ are as defined herein, and $Z^1$, $Z^2$, $Z^3$, $Z^4$, $Z^5$, and $Z^6$ are as defined below.

Compound Vc with Compound Vd) or conditions known in the art. In Compound Ve, $Z^4$ may be a suitable leaving group for a cross coupling reaction (e.g., a halo such as a chloro). In Compound Ve, $Z^5$ may be a suitable leaving group for an amide bond forming reaction (e.g., a hydroxyl or a halo such as a chloro, or a pseudohalide such as a sulfonyl). In Compound Vf, $Z^6$ may be a suitable coupling partner (e.g., for metal-catalyzed cross coupling) for attaching $X^1$ (e.g., a boronic acid or boronic ester).

In Scheme 1, Compound Vg may be reacted with Compound Vh to form a compound of Formula I under suitable conditions for amide bond formation, for example, conditions described herein (e.g., with respect to reaction of Compound Va with Compound Vb) or conditions known in the art.

A person of skill in the art will appreciate that any of Compound Va, Vb, Vc, Vd, Ve, Vf, Vg, or Vh may be available from a commercial supplier for a particular embodiment. Alternative synthesis of Compound Va, Vb, Vc, Vd, Ve, Vf, Vg, or Vh may be as described herein or as known to those of skill in the art.

EXAMPLES

General Experimental Procedures

Commercially available reagents and solvents (HPLC grade) were used without further purification. $^1$H NMR spectra were recorded on a Bruker DRX 500 MHz spectrometer, a Bruker DPX 250 MHz spectrometer, a Bruker AVANCE 300 300 MHz spectrometer or a Bruker AVANCE 500 500 MHz spectrometer in deuterated solvents. Chemical shifts (δ) are in parts per million. Flash column chromatography refers to automated purification on Biotage Isolera systems using appropriately sized SNAP or KPNH prepacked silica columns, or on Isco Combiflash Rf systems using pre-packed silica columns and the solvents recorded in the experimental section. Thin-layer chromatography (TLC) analysis was performed with Kieselgel 60 F254 (Merck) plates and visualized using UV light. SCX chromatography was performed with Biotage Isolute Flash SCX-2 loading the sample in methanol and eluting with methanol then 5% ammonia in methanol.

Acidic Phase HPLC Methods

Analytical HPLC-MS method 1 was performed on Shimadzu LCMS-2010EV systems using a reverse phase Supelco Ascentis Express column (2.7 μm, 2.1×30 mm), gradient 5-100% B (A=water/0.1% formic acid, B=acetonitrile/0.1% formic acid) at a column temp of 40° C. over 1.5 min then 100% B for 0.1 min, injection volume 3 μL, flow=1.0 mL/min. UV spectra were recorded at 215 nm using a SPD-M20A photo diode array (PDA) detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, HPLC-MS method 2 was performed on Shimadzu LCMS-2010EV systems using a reverse phase Kinetix Core-Shell C18 column (5 μm, 2.1×50 mm) at a column temp of 40° C., gradient 5-100% B (A=water/0.1% formic acid, B=acetonitrile/0.1% formic acid) over 1.2 min, then 100% B over 0.1 min, injection volume 3 μL, flow=1.2 mL/min. All other aspects of the method were unchanged.

Alternatively, analytical HPLC-MS method 3 was performed on Shimadzu LCMS-2010EV systems using reverse phase Waters Atlantis dC18 columns (3 μm, 2.1×100 mm), gradient 5-100% B (A=water/0.1% formic acid, B=acetonitrile/0.1% formic acid) at a column temp of 40° C. over 2.5 min then 100% B for 0.2 min, injection volume 3 μL, flow=1.0 mL/min. UV spectra were recorded at 215 nm using a SPD-M20A PDA detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, analytical HPLC-MS method 4 was performed on Shimadzu LCMS-2010EV systems using reverse phase Waters Atlantis dC18 columns (3 μm, 2.1×100 mm), gradient 5-100% B (A=water/0.1% formic acid, B=acetonitrile/0.1% formic acid) at a column temp of 40° C. over 5.0 min then 100% B for 0.4 min, injection volume 3 μL, flow=0.6 mL/min. UV spectra were recorded at 215 nm using a SPD-M20A PDA detector. Mass spectra were obtained over the range m/z 100 to 1000 at a sampling rate of 2 scans per second using a LCMS2010EV. Data were integrated and reported using Shimadzu LCMS-Solutions and PsiPort software.

Alternatively, analytical HPLC-MS method 5 was performed on a Waters Acquity UPLC system with Waters PDA and ELS detectors using a Phenomenex Kinetex-XB C-18 column, (1.7 μm, 2.1 mm×100 mm at a column temp of 40° C., gradient 5-100% B (A=water/0.1% formic acid; B=acetonitrile/0.1% formic acid) over 5.3 min, then 100% B for 0.5 min, flow=0.6 ml/min. UV spectra were recorded at 215 nm using a Waters Acquity PDA detector. Mass spectra were obtained over the range m/z 150 to 850 at a sampling rate of 2 scans per second using a Waters ZQ. Data were integrated and reported using OpenLynx software.

Alternatively, analytical HPLC method 6 was performed on a Varian Pro Star 210 system using an XBridge C18 column (3.5 μm, 4.6×150 mm), gradient 5-100% B (A=water/0.1% trifluoroacetic acid, B=acetonitrile/0.1% trifluoroacetic acid) at an ambient column temp (approx. 22° C.) over 20.0 min then 100% B for 1.0 min, flow=1.0 mL/min. UV spectra were recorded at 254 and 215 nm using a Varian Pro Star 330 (PDA) detector.

Alternatively, UHPLC method 7 UHPLC method 7 was performed on a Waters Acquity H-Class system using an Acquity UPLC BEH C18 column (1.7 μm, 2.1×75 mm), gradient 5-100% B (A=water/0.1% trifluoroacetic acid, B=acetonitrile/0.1% trifluoroacetic acid) at an ambient column temp (approx. 22° C.) over 6.0 min then 100% B for 2.0 min, flow=0.5 mL/min. UV spectra were recorded at 254 and 215 nm.

Alternatively, mass spectra and LCMS analyses were obtained using a Waters Acquity SQD (ESI, UP-LCMS) system or an Agilent G6100A SQ LCMS System.

Basic Phase HPLC Methods

Analytical HPLC-MS method 8 was performed on Hewlett Packard HPLC systems using reverse phase Phenomenex Gemini C18 columns (3 μm, 2.0×50 mm), at a column temp of 60° C.; gradient 1-100% B (A=2 mM ammonium bicarbonate in water buffered to pH 10, B=acetonitrile) over 1.8 min then 100% B for 0.3 min, injection volume 3 μL, flow=1 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

Analytical HPLC-MS (HPLC-MS method 5) was performed on Hewlett Packard HPLC systems using reverse phase Phenomenex Gemini C18 columns (3 μm, 2.0×100 mm), gradient 5-100% B (A=2 mM ammonium bicarbonate in water buffered to pH 10, B=acetonitrile) over 5.5 min then 100% B for 0.4 min, injection volume 3 μL, flow=0.5 mL/minute. UV spectra were recorded at 215 nm using a Waters PDA detector. Mass spectra were obtained over the range m/z 150 to 850 at a sampling rate of 2 scans per second using a Waters ZQ. Data were integrated and reported using OpenLynx software.

HPLC-MS method 5 was subsequently replaced with the HPLC-MS method 9 where the flow rate increased to 0.6 mL/min. All other parameters were unchanged.

Alternatively, analytical HPLC-MS method 10 was performed on a Waters Acquity UPLC system with Waters PDA and ELS detectors using a Waters UPLC® CSH™ (1.7 μm, 2.1×100 mm) column, at a column temp of 40° C.; gradient 5-100% B (A=2 mM ammonium bicarbonate in water buffered to pH 10, B=acetonitrile) over 5.3 min then 100% B for 0.5 min, injection volume 1 μL, flow=0.6 mL/minute. UV spectra were recorded at 215 nm using a Waters Acquity PDA detector. Mass spectra were obtained over the range m/z 150 to 850 at a sampling rate of 2 scans per second using a Waters Quattro Premier XE. Data were integrated and reported using OpenLynx software.

All example compounds display an LC purity of >95% unless stated otherwise.

Method 1
Scheme for Method 1

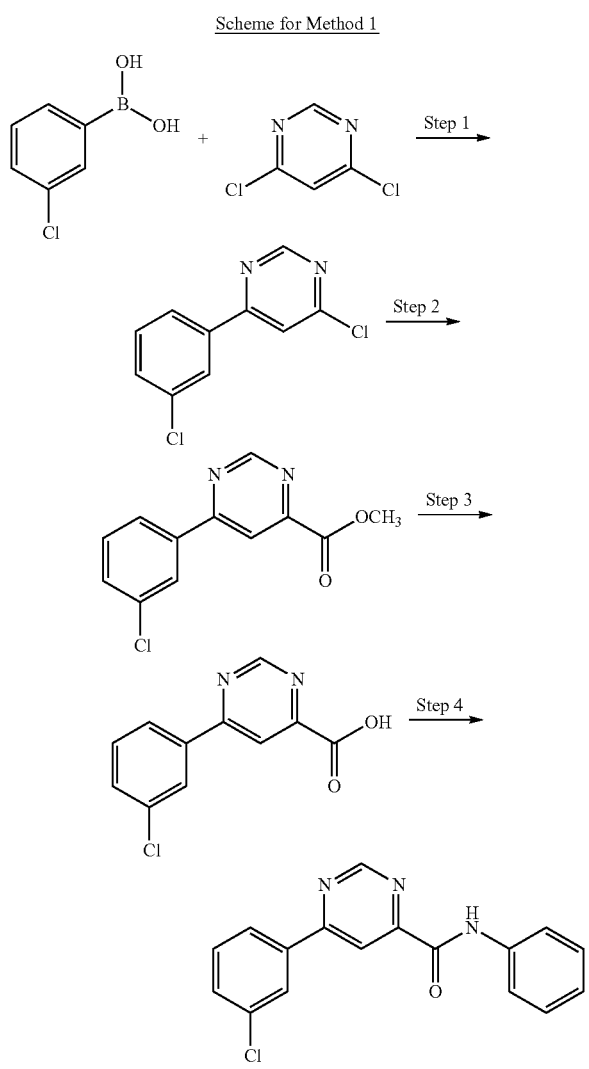

Example 1

Example 1: 6-(3-Chlorophenyl)-N-phenylpyrimidine-4-carboxamide

Step 1: 4-Chloro-6-(3-chlorophenyl)pyrimidine

3-Chlorophenyl boronic acid (10.0 g, 64 mmol) and Pd(PPh$_3$)$_4$ (4.23 g, 3.6 mmol) were added to a stirred suspension of 4,6-dichloropyrimidine (13.6 g, 91 mmol) in 1,4-dioxane (160 mL). A 2M K$_2$CO$_3$ solution (80 mL) was added to the resulting mixture, which was heated at 90° C. for 1.5 h under an atmosphere of N$_2$. The reaction mixture was cooled to room temperature and concentrated in vacuo. The residue was dissolved in DCM (500 mL) and washed with water (200 mL). The aqueous phase was back-extracted with DCM (200 mL) and the combined organic extracts were washed with brine (200 mL). The organic layer was concentrated in vacuo. The resulting residue was purified by column chromatography (silica, 5% EtOAc in heptane) to give the title compound. Tr(HPLC-MS method 3)=2.15 min m/z (ES$^+$) (M+H)$^+$ 225.0.

Step 2: Methyl 6-(3-chlorophenyl)pyrimidine-4-carboxylate

4-Chloro-6-(3-chlorophenyl)pyrimidine (4.6 g, 20.3 mmol), PdCl$_2$(dppf)-DCM (830 mg, 1.0 mmol) and triethylamine (5.65 mL, 40.5 mmol) were suspended in degassed MeOH (200 mL) in a pressure vessel fitted with a magnetic stirrer bar. The atmosphere in the reaction vessel was replaced with N$_2$ by successive evacuation and charging with N$_2$ gas (this process was repeated three times). The vessel was then flushed with CO by successive charging with CO and evacuation. The vessel was pressurized to 5 bar of CO and heated at 50° C. with stirring for 3 hours. The reaction vessel was allowed to cool to room temperature before venting CO and flushing with N$_2$. The reaction mixture was concentrated in vacuo and the resulting residue dissolved in EtOAc (30 vol) and water (30 vol). The solution was filtered through cotton wool and the organic layer was separated, and concentrated under reduced pressure. The aqueous layer was back-extracted with DCM, the organic layer separated and concentrated in vacuo. Residues of both extracts were combined with a repeat run (on equivalent scale). Purification by column chromatography (silica, 0-20% EtOAc-heptane) gave the title compound. Tr(HPLC-MS method 3)=1.99 min m/z (ES$^+$) (M+H)$^+$ 250.0.

Step 3: 6-(3-Chlorophenyl)pyrimidine-4-carboxylic acid

Methyl 6-(3-chlorophenyl)pyrimidine-4-carboxylate (8.65 g, 34.8 mmol) was suspended in THF (100 mL) and 1 M NaOH (100 mL) and stirred at room temperature for 30 min. The THF was removed in vacuo, and the aqueous layer containing suspended solid was adjusted to pH 1 using conc. HCl. MeCN (300 mL) was added and the mixture heated to 90° C. for 90 min. The mixture was cooled to rt and the solid collected by filtration and dried in vacuo to give the title compound. $^1$H NMR (500 MHz, DMSO-d$_6$) δ 9.40 (m, 1H), 8.55 (m, 1H), 8.35 (m, 1H), 8.25 (m, 1H), 7.70-7.51 (m, 2H). Tr(HPLC-MS method 3)=1.82 min m/z (ES$^+$) (M+H)$^+$ 235.0.

Step 4: 6-(3-Chlorophenyl)-N-phenylpyrimidine-4-carboxamide 6-(3-Chlorophenyl)pyrimidine-4-carboxylic acid (200 mg, 0.85 mmol) was dissolved in DMF (4 mL). EDC-hydrochloride (243 mg, 1.3 mmol) and HOBt (115 mg, 0.85 mmol) were added and the mixture was stirred at rt for 1 h. Aniline (80 mg, 0.85 mmol) was added and the mixture stirred at rt overnight. Additional EDC-hydrochloride (81 mg, 0.42 mmol) was added and the mixture heated to 50° C. for 1 h., then the mixture was cooled to rt, and diluted with water (4 mL). DCM (10 mL) was added and the mixture shaken, then the organic layer was separated. The organic layer was washed with water (5 mL) and brine (5 mL), then concentrated in vacuo. The resulting solid was washed with water (3×5 mL) and dried in vacuo to give the title compound. Tr(HPLC-MS method 4)=5.17 min m/z (ES$^+$) (M+H)$^+$ 309.9.

Also prepared by this route:

| Ex. | Structure | LCMS data |
|---|---|---|
| 2 | (structure) | Tr(HPLC-MS method 4) = 4.57 min m/z (ES$^+$) (M + H)$^+$ 336.1. |
| 3 | (structure) | Tr(HPLC-MS method 4) = 4.15 min m/z (ES$^+$) (M + H)$^+$ 341.1. |

Method 2

Scheme for Method 2

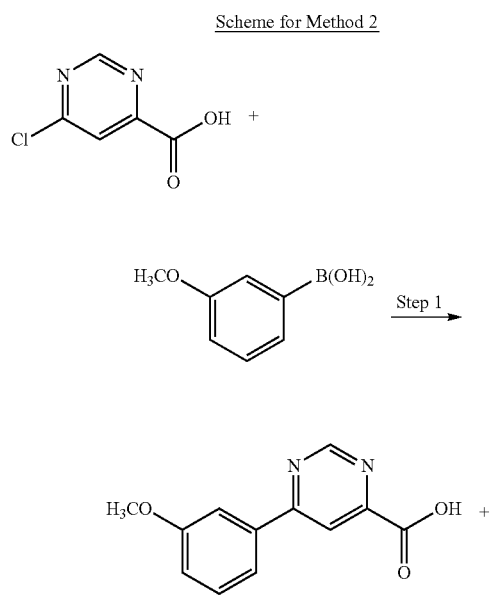

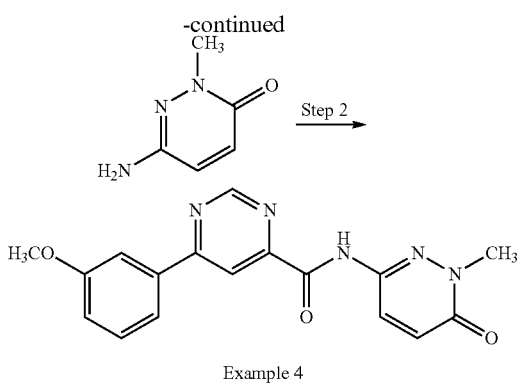

Example 4

Example 4: 6-(3-Methoxyphenyl)-N-(1-methyl-6-oxo-1,6-dihydropyridazin-3-yl)pyrimidine-4-carboxamide Step 1:
6-(3-Methoxyphenyl)pyrimidine-4-carboxylic acid A mixture of 6-chloropyrimidine-4-carboxylic acid (157 mg, 0.987 mmol), (3-methoxyphenyl)boronic acid (150 mg, 0.987 mmol), potassium phosphate tribasic (629 mg, 2.96 mmol) and dichloro[1,1'-bis(diphenylphosphino)ferrocene]palladium(II) dichloromethane adduct (40 mg, 0.049 mmol) in MeCN (1.0 mL) and water (1.0 mL) was heated at 60° C. for 2 h. After this time, the crude product mixture was adsorbed onto silica gel and purified by FCC (Silica, 0-100% MeOH in DCM) to give the title compound. $^1$H NMR (300 MHz, DMSO-d$_6$) δ 12.17 (br s, 1H), 9.14 (d, J=0.9 Hz, 1H), 8.17 (s, 1H), 7.78-7.70 (m, 2H), 7.45 (t, J=8.1 Hz, 1H), 7.11 (dd, J=7.5, 1.8 Hz, 1H), 3.85 (s, 3H).

Step 2: 6-(3-Methoxyphenyl)-N-(1-methyl-6-oxo-1,6-dihydropyridazin-3-yl)pyrimidine-4-carboxamide EDC (170 mg, 0.886 mmol) was added to a mixture of 6-(3-methoxyphenyl)pyrimidine-4-carboxylic acid (136 mg, 0.591 mmol) and 6-amino-2-methylpyridazin-3(2H)-one (74 mg, 0.59 mmol) in anhydrous pyridine (2 mL), and the resulting reaction mixture was stirred at rt for 16 h. After this time, the mixture was diluted with water (10 mL) and EtOAc (10 mL). The layers were separated, and the organic layer was washed with brine, dried over Na$_2$SO$_4$, filtered, and the filtrate concentrated under reduced pressure. The residue obtained was purified by FCC (Silica, 0-100% EtOAc in DCM), and the product obtained was recrystallized from MeCN to give the title compound. $^1$H NMR (500 MHz, DMSO-d$_6$) δ 10.90 (s, 1H), 9.44 (d, J=1.5 Hz, 1H), 8.58 (d, J=1.5 Hz, 1H), 8.01 (d, J=10.0 Hz, 1H), 7.92-7.87 (m, 1H), 7.83 (t, J=2.5 Hz, 1H), 7.51 (t, J=8.0 Hz, 1H), 7.22-7.17 (m, 1H), 7.08 (d, J=9.5 Hz, 1H), 3.88 (s, 3H), 3.64 (s, 3H). Tr (HPLC method 6)=14.11 min. m/z (ES$^+$) (M+H)$^+$ 338.1.

Also prepared by this route:

| Ex. | Structure | LC and MS data |
|---|---|---|
| 5 | 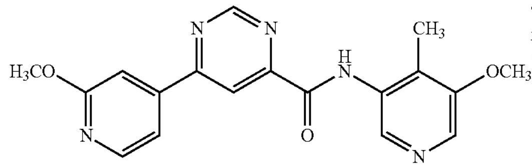 [SMILES: COc1cc(-c2cc(C(=O)Nc3cncc(OC)c3C)ncn2)ccn1] | Tr (UHPLC method 7UHPLC method 7) = 3.13 min, m/z (ES$^+$) (M + H)$^+$ 352.2. |
| 6 | 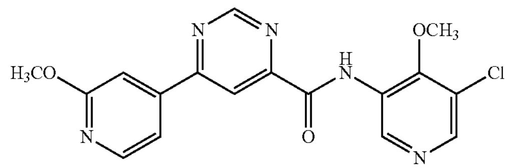 [SMILES: COc1cc(-c2cc(C(=O)Nc3cncc(Cl)c3OC)ncn2)ccn1] | Tr (UHPLC method 7UHPLC method 7) = 3.54 mm, m/z (ES$^+$) (M + H)$^+$ 372.1. |
| 7 | 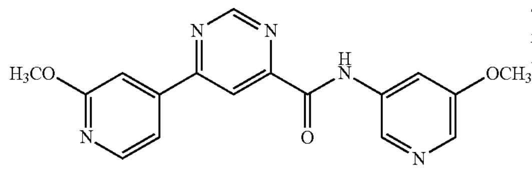 [SMILES: COc1cncc(NC(=O)c2cc(-c3ccnc(OC)c3)ncn2)c1] | Tr (UHPLC method 7) = 3.01 min, m/z (ES$^+$) (M + H)$^+$ 338.1. |

Method 3

Scheme for Method 3

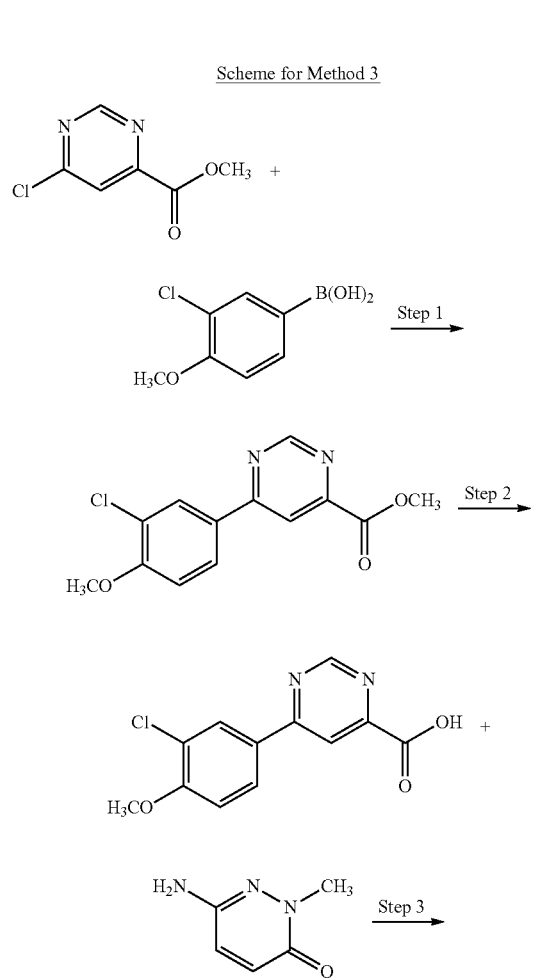

Scheme for Method 3

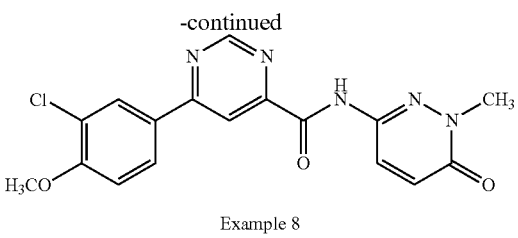

Example 8

Example 8: 6-(3-Chloro-4-methoxyphenyl)-N-(1-methyl-6-oxo-1,6-dihydropyridazin-3-yl)pyrimidine-4-carboxamide Step 1: Methyl 6-(3-chloro-4-methoxyphenyl)pyrimidine-4-carboxylate A mixture of methyl 6-chloropyrimidine-4-carboxylate (200 mg, 1.16 mmol), (3-chloro-4-methoxy-phenyl)boronic acid (432 mg, 2.32 mmol), dichloro[1,1′-bis(diphenylphosphino)ferrocene]palladium dichloromethane adduct (85 mg, 0.12 mmol) and potassium phosphate (738 mg, 3.48 mmol) in DMF (10 mL) was purged with argon and heated in a sealed tube at 60° C. for 3 h. After this time, the reaction mixture was concentrated under reduced pressure, and the residue obtained was purified by FCC (Silica, 0-5% MeOH in DCM) to give the title compound. m/z (ES$^+$) (M+H)$^+$ 279.0. $^1$H NMR (300 MHz, DMSO-d$_6$) δ 9.35 (d, J=1.2 Hz, 1H), 8.53 (d, J=1.2 Hz, 1H), 8.39 (d, J=2.1 Hz, 1H), 8.31 (dd, J=8.7, 2.4 Hz, 1H), 7.34 (d, J=9.0 Hz, 1H), 3.97 (s, 3H), 3.95 (s, 3H).

Step 2: 6-(3-Chloro-4-methoxyphenyl)pyrimidine-4-carboxylic acid

Lithium hydroxide (18 mg, 0.44 mmol) was added to a solution of methyl 6-(3-chloro-4-methoxyphenyl)pyrimidine-4-carboxylate (122 mg, 0.438 mmol) in THF (1.2 mL) and water (1.2 mL), and the mixture was stirred at rt for 2 h. After this time, the solvent was removed under reduced pressure, and water was added. The mixture was acidified to pH 2 with 2N HCl. The resulting precipitate was collected by filtration, washed with water, and dried under reduced pressure to give the title compound. m/z (ES+) (M+H)+ 265.0. $^1$H NMR (300 MHz, DMSO-d$_6$) δ 13.94 (br s, 1H), 9.34 (d, J=0.9 Hz, 1H), 8.49 (d, J=0.9 Hz, 1H), 8.38 (d, J=2.1 Hz, 1H), 8.30 (dd, J=8.7, 2.1 Hz, 1H), 7.33 (d, J=8.7 Hz, 1H), 3.96 (s, 3H).

Step 3: 6-(3-Chloro-4-methoxyphenyl)-N-(1-methyl-6-oxo-1,6-dihydropyridazin-3-yl)pyrimidine-4-carboxamide HATU (480 mg, 1.26 mmol) was added to a mixture of 6-(3-chloro-4-methoxyphenyl)pyrimidine-4-carboxylic acid (167 mg, 0.631 mmol), 6-amino-2-methylpyridazin-3(2H)-one (79 mg, 0.63 mmol) and DIPEA (0.33 mL, 1.9 mmol) in DMF (12 mL), and the mixture was stirred at rt for 16 h. After this time, water (50 mL) was added, and the resulting precipitate was isolated by filtration to give the title compound. $^1$H NMR (300 MHz, DMSO-d$_6$) δ 10.89 (s, 1H), 9.38 (d, J=1.2 Hz, 1H), 8.58 (d, J=1.2 Hz, 1H), 8.41 (d, J=2.1 Hz, 1H), 8.34 (dd, J=10.8, 2.1 Hz, 1H), 8.02 (d, J=9.9 Hz, 1H), 7.35 (d, J=8.7 Hz, 1H), 7.09 (d, J=9.9 Hz, 1H), 3.97 (s, 3H), 3.64 (s, 3H). Tr (UHPLC method 7)=4.42 min. m/z (ES+) (M+H+) 372.0.

Also prepared by this route (in some instances, in Step 3, a suitable coupling agent was used (for example, EDC)):

| Ex. | Structure | LCMS data |
|---|---|---|
| 9 | 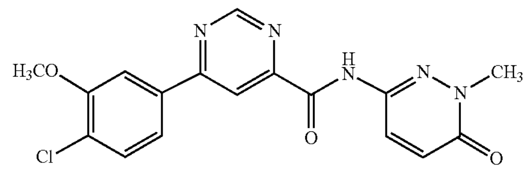 [SMILES: COc1cc(-c2cc(C(=O)Nc3ccc(=O)n(C)n3)ncn2)ccc1Cl] | Tr (UHPLC method 7) = 4.45 min, m/z (ES+) (M + H)+ 372.0. |
| 10 | 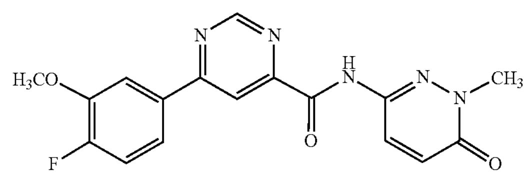 [SMILES: COc1cc(-c2cc(C(=O)Nc3ccc(=O)n(C)n3)ncn2)ccc1F] | Tr (UHPLC method 7) = 4.08 min, m/z (ES+) (M + H)+ 356.1. |
| 11 | 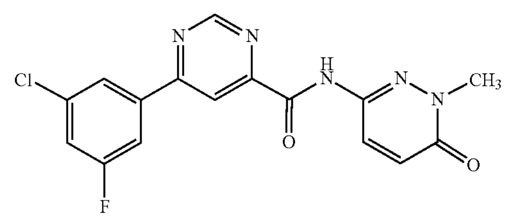 [SMILES: Cn1nc(NC(=O)c2cc(-c3cc(F)cc(Cl)c3)ncn2)ccc1=O] | Tr (UHPLC method 7) = 4.72 min, m/z (ES+) (M + H)+ 360.0. |
| 12 | 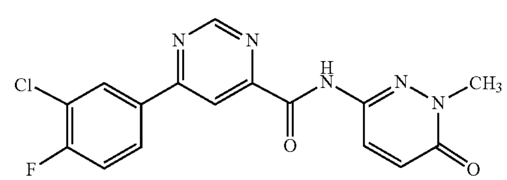 [SMILES: Cn1nc(NC(=O)c2cc(-c3ccc(F)c(Cl)c3)ncn2)ccc1=O] | Tr (UHPLC method 7) = 4.63 min, m/z (ES+) (M + H)+ 360.0. |
| 13 | 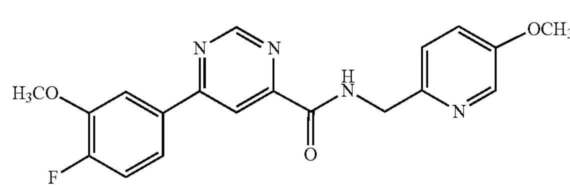 [SMILES: COc1ccc(CNC(=O)c2cc(-c3ccc(F)c(OC)c3)ncn2)nc1] | Tr (UHPLC method 7) = 3.55 min, m/z (ES+) (M + H)+ 369.1. |
| 14 | 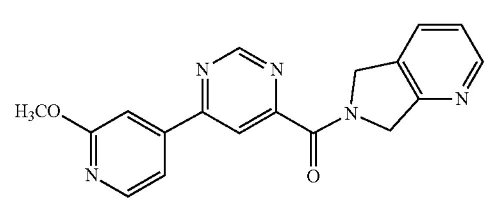 [SMILES: COc1cc(-c2cc(C(=O)N3Cc4cccnc4C3)ncn2)ccn1] | Tr (UHPLC method 7) = 3.03 min, m/z (ES+) (M + H)+ 334.0. |

-continued
| Ex. | Structure | LCMS data |
|---|---|---|
| 15 | 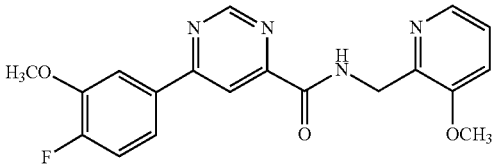 [SMILES: COc1cc(-c2cc(C(=O)NCc3ncccc3OC)ncn2)ccc1F] | Tr (UHPLC method 7) = 3.69 min, m/z (ES+) (M + H)+ 369.1. |
| 16 | 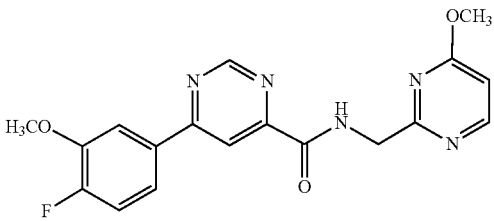 [SMILES: COc1ccnc(CNC(=O)c2cc(-c3ccc(F)c(OC)c3)ncn2)n1] | Tr (UHPLC method 7) = 4.36 min, m/z (ES+) (M + H)+ 370.2. |
| 17 | 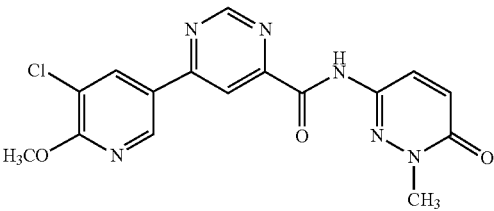 [SMILES: COc1ncc(-c2cc(C(=O)Nc3ccc(=O)n(C)n3)ncn2)cc1Cl] | Tr (UHPLC method 7) = 4.89 min, m/z (ES+) (M + H)+ 373.0. |
| 18 | 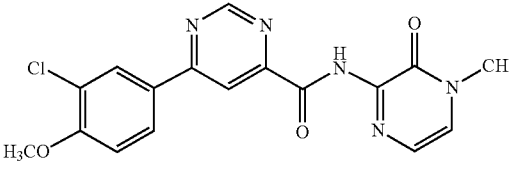 | Tr (UHPLC method 7) = 4.76 min, m/z (ES+) (M + H)+ 372.1. |
| 19 | 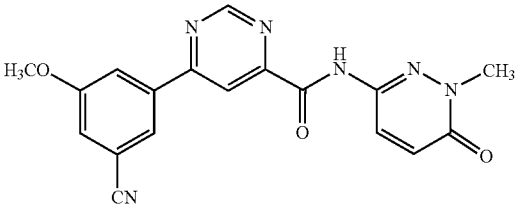 [SMILES: COc1cc(C#N)cc(-c2cc(C(=O)Nc3ccc(=O)n(C)n3)ncn2)c1] | Tr (UHPLC method 7) = 4.77 min, m/z (ES−) (M − H)− 361.4. |
| 20 | 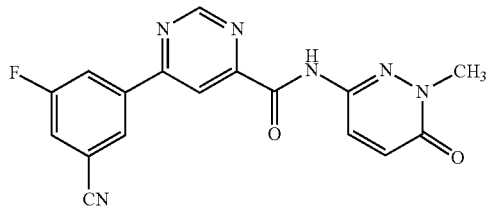 [SMILES: Cn1nc(NC(=O)c2cc(-c3cc(F)cc(C#N)c3)ncn2)ccc1=O] | Tr (UHPLC method 7) = 3.94 min, m/z (ES+) (M + H)+ 351.0. |
| 21 | 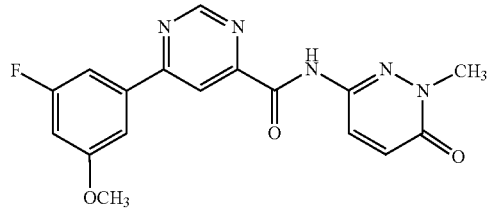 | Tr (UHPLC method 7) = 4.28 min, m/z (ES+) (M + H)+ 356.1. |

-continued

| Ex. | Structure | LCMS data |
|---|---|---|
| 22 | 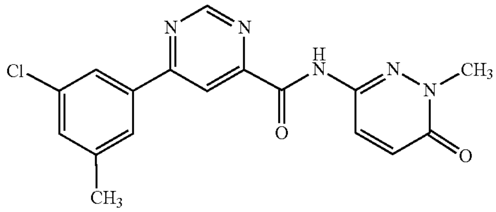 [SMILES: Cc1cc(Cl)cc(-c2cc(C(=O)Nc3ccc(=O)n(C)n3)ncn2)c1] | Tr (UHPLC method 7) = 4.94 min, m/z (ES⁻) (M − H)⁻ 354.2. |
| 23 | 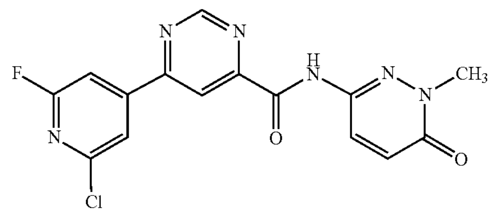 [SMILES: Cn1nc(NC(=O)c2cc(-c3cc(F)nc(Cl)c3)ncn2)ccc1=O] | Tr (UHPLC method 7) = 5.30 min, m/z (ES⁺) (M + H)⁺ 361.0. |
| 24 | 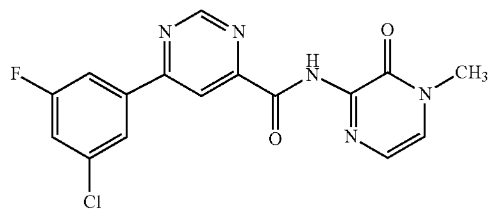 [SMILES: Cn1ccnc(NC(=O)c2cc(-c3cc(F)cc(Cl)c3)ncn2)c1=O] | Tr (UHPLC method 7) = 5.64 min, m/z (ES⁺) (M + H)⁺ 360.1. |
| 25 | 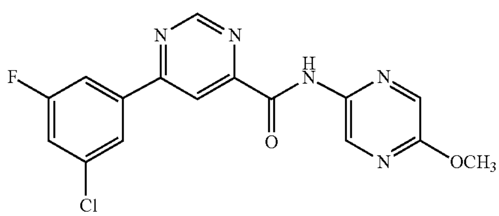 [SMILES: COc1cnc(NC(=O)c2cc(-c3cc(F)cc(Cl)c3)ncn2)cn1] | Tr (UHPLC method 7) = 6.06 min, m/z (ES⁺) (M + H)⁺ 360.0. |
| 26 | 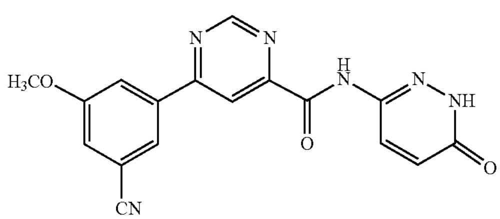 [SMILES: COc1cc(C#N)cc(-c2cc(C(=O)Nc3ccc(=O)[nH]n3)ncn2)c1] | Tr (UHPLC method 7) = 5.08 min, m/z (ES⁺) (M + H)⁺ 349.0. |
| 27 | 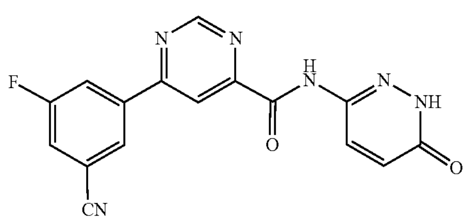 [SMILES: N#Cc1cc(F)cc(-c2cc(C(=O)Nc3ccc(=O)[nH]n3)ncn2)c1] | Tr (UHPLC method 7) = 4.68 min, m/z (ES⁺) (M + H)⁺ 337.0. |
| 28 | 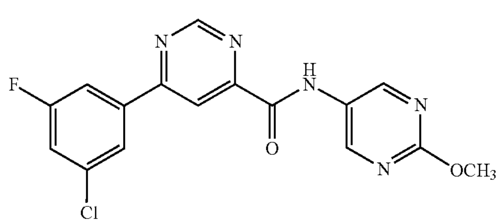 [SMILES: COc1ncc(NC(=O)c2cc(-c3cc(F)cc(Cl)c3)ncn2)cn1] | Tr (UHPLC method 7) = 5.99 min, m/z (ES⁺) (M + H)⁺ 360.1. |

| Ex. | Structure | LCMS data |
|---|---|---|
| 41 | 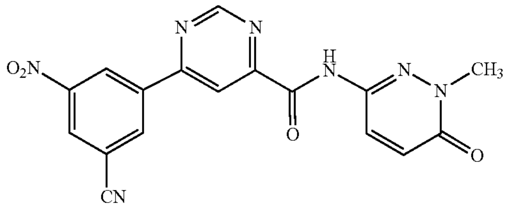 [SMILES: Cn1nc(NC(=O)c2cc(-c3cc(C#N)cc([N+](=O)[O-])c3)ncn2)ccc1=O] | Tr (UHPLC method 7) = 3.53 min, m/z (ES+) (M + H)+ 378.0. |

Method 4

Scheme for Method 4

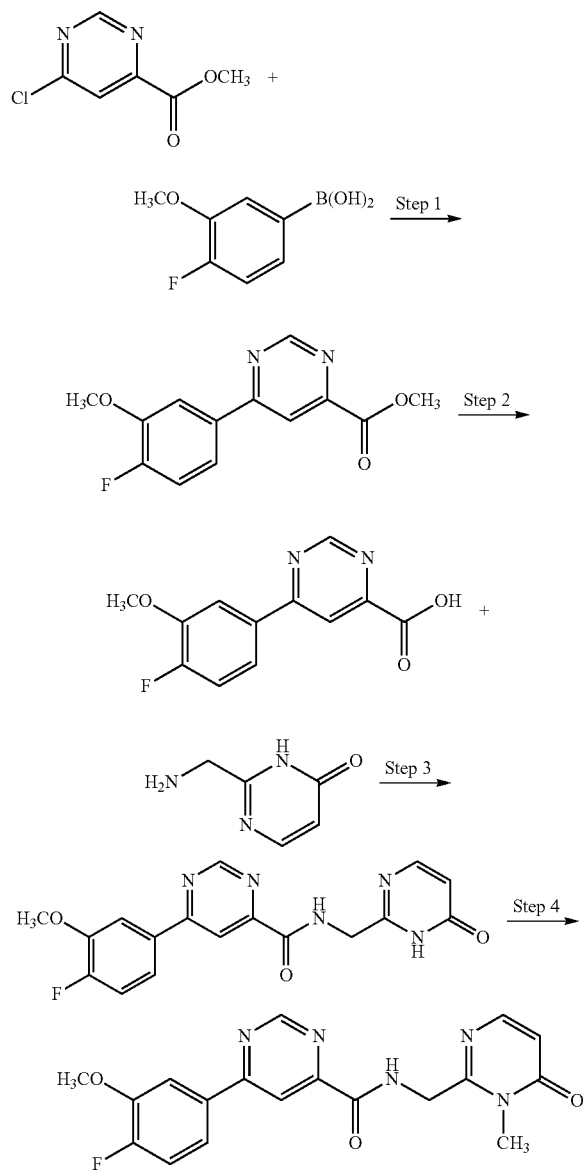

Example 29

Example 29: 6-(4-Fluoro-3-methoxyphenyl)-N-((1-methyl-6-oxo-1,6-dihydropyrimidin-2-yl)methyl)pyrimidine-4-carboxamide Step 1: Methyl 6-(4-fluoro-3-methoxyphenyl)pyrimidine-4-carboxylate A mixture of methyl 6-chloropyrimidine-4-carboxylate (250 mg, 1.45 mmol), (4-fluoro-3-methoxyphenyl)boronic acid (492 mg, 2.90 mmol), dichloro[1,1'-bis(diphenylphosphino)ferrocene]palladium dichloromethane adduct (106 mg, 0.145 mmol) and potassium phosphate (923 mg, 4.35 mmol) in DMF (12.5 mL) was purged with argon and heated in a sealed tube at 60° C. for 3 h. After this time, the reaction mixture was concentrated under reduced pressure. The residue obtained was partitioned between EtOAc (50 mL) and water (50 mL), and the layers were separated. The aqueous layer was extracted with EtOAc (2×100 mL), and the combined organic layers were washed with water (100 mL) and brine (100 mL), dried over $Na_2SO_4$, filtered, and concentrated under reduced pressure. The residue obtained was purified twice by FCC (Silica, 0-5% MeOH in DCM) to give the title compound. m/z (ES+) (M+H)+ 263.1. $^1$H NMR (300 MHz, DMSO-$d_6$) δ 9.41 (d, J=1.5 Hz, 1H), 8.59 (d, J=1.2 Hz, 1H), 8.03 (dd, J=8.4, 2.1 Hz, 1H), 7.96-7.91 (m, 1H), 7.42 (dd, J=11.1, 8.4 Hz, 1H), 3.98 (s, 3H), 3.96 (s, 3H).

Step 2: 6-(4-Fluoro-3-methoxyphenyl)pyrimidine-4-carboxylic acid

Lithium hydroxide monohydrate (3.4 mg, 0.081 mmol) was added to a solution of methyl 6-(4-fluoro-3-methoxyphenyl)pyrimidine-4-carboxylate (21 mg, 0.080 mmol) in THF (0.5 mL) and water (0.5 mL), and the mixture was stirred at rt for 2 h. After this time, the solvent was removed under reduced pressure, and water was added. The mixture was acidified to pH 2 with 2N HCl. The precipitate was collected by filtration, washed with water, and dried under reduced pressure to give the title compound. m/z (ES+) (M+H)+ 249.1. $^1$H NMR (300 MHz, DMSO-$d_6$) δ 14.00 (br s, 1H), 9.39 (d, J=1.2 Hz, 1H), 8.56 (d, J=1.2 Hz, 1H), 8.03 (dd, J=8.4, 2.1 Hz, 1H), 7.95-7.90 (m, 1H), 7.42 (dd, J=11.4, 8.7 Hz, 1H), 3.98 (s, 3H).

Step 3: 6-(4-Fluoro-3-methoxyphenyl)-N-((6-oxo-1,6-dihydropyrimidin-2-yl)methyl)pyrimidine-4-carboxamide HATU (245 mg, 0.645 mmol) was added to a mixture of 6-(4-fluoro-3-methoxyphenyl)pyrimidine-4-carboxylic acid (80 mg, 0.32 mmol), 2-(aminomethyl)pyrimidin-4(3H)-one dihydrochloride (64 mg, 0.32 mmol) and DIPEA (0.28 mL, 1.6 mmol) in DMF (6 mL), and the mixture was stirred at rt for 3 d. After this time, water (50 mL) was added, and the resulting precipitate was collected by filtration and purified by FCC (Silica, 0-10% MeOH in DCM) to give the title compound. m/z (ES$^+$) (M+H)$^+$ 356.1. $^1$H NMR (300 MHz, DMSO-d$_6$) δ 12.59 (br s, 1H), 9.42-9.38 (m, 2H), 8.57 (d, J=1.2 Hz, 1H), 8.04 (dd, J=8.4, 2.1 Hz, 1H), 7.96-7.91 (m, 1H), 7.87 (d, J=6.3 Hz, 1H), 7.42 (dd, J=11.1, 8.7 Hz, 1H), 6.23 (d, J=6.0 Hz, 1H), 4.45 (d, J=5.7 Hz, 2H), 3.98 (s, 3H).

Step 4: 6-(4-Fluoro-3-methoxyphenyl)-N-((1-methyl-6-oxo-1,6-dihydropyrimidin-2-yl)methyl)pyrimidine-4-carboxamide Potassium carbonate (23 mg, 0.16 mmol) and iodomethane (0.03 mL, 0.4 mmol) were added to a solution of 6-(4-fluoro-3-methoxyphenyl)-N-((6-oxo-1,6-dihydropyrimidin-2-yl)methyl)pyrimidine-4-carboxamide (53 mg, 0.15 mmol) in DMF (3.3 mL), and the mixture was stirred at rt for 4 h. After this time, water (25 mL) was added, and the reaction mixture was extracted with EtOAc (50 mL). The organic layer was washed with brine (25 mL), dried over Na$_2$SO$_4$, filtered, and concentrated. The residue obtained was purified by FCC (Silica, 40-60% EtOAc in DCM, then 0-10% MeOH in DCM) to give the title compound. This material was combined with a previous batch and dissolved in DCM (20 mL), washed with an aq 10% sodium thiosulfate solution (20 mL) and brine, dried over Na$_2$SO$_4$, filtered, and concentrated. The material obtained was triturated in MeCN at 82° C. and lyophilized four times to give the title compound. $^1$H NMR (300 MHz, DMSO-d$_6$) δ 9.43-9.39 (m, 2H), 8.60 (d, J=1.2 Hz, 1H), 8.06 (dd, J=8.7, 2.4 Hz, 1H), 7.98-7.92 (m, 2H), 7.43 (dd, J=11.1, 8.7 Hz, 1H), 6.38 (d, J=6.6 Hz, 1H), 4.70 (d, J=5.1 Hz, 2H), 3.99 (s, 3H), 3.50 (s, 3H). Tr (UHPLC method 7)=3.84 min. m/z (ES$^+$) (M+H)$^+$ 370.2.

Also prepared by this route:

Method 5
Scheme for Method 5

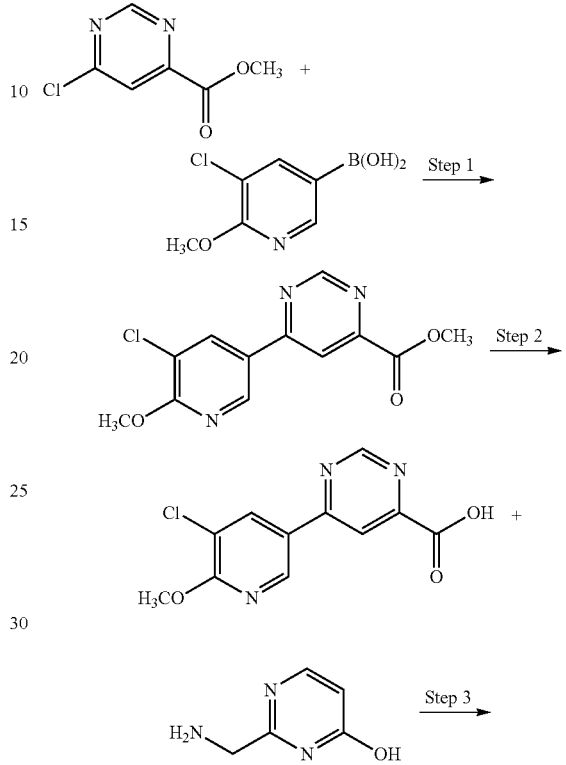

| Ex. | Structure | LCMS data |
|---|---|---|
| 30 | 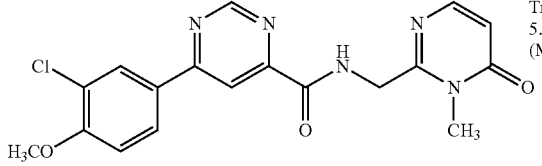 | Tr (UHPLC method 7) = 5.25 min, m/z (ES$^+$) (M + H)$^+$ 386.1. |
| 31 | 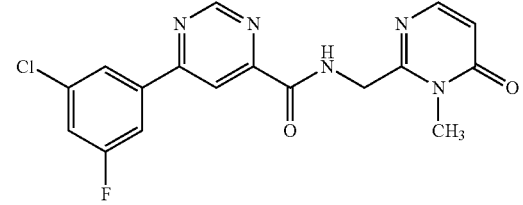 [SMILES: Cn1c(CNC(=O)c2cc(-c3cc(F)cc(Cl)c3)ncn2)nccc1=O] | Tr (UHPLC method 7) = 5.67 min, m/z (ES$^+$) (M + H)$^+$ 374.1. |
| 32 | 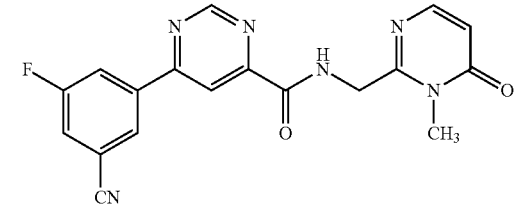 [SMILES: Cn1c(CNC(=O)c2cc(-c3cc(F)cc(C#N)c3)ncn2)nccc1=O] | Tr (UHPLC method 7) = 3.66 min, m/z (ES$^+$) (M + H)$^+$ 365.1. |

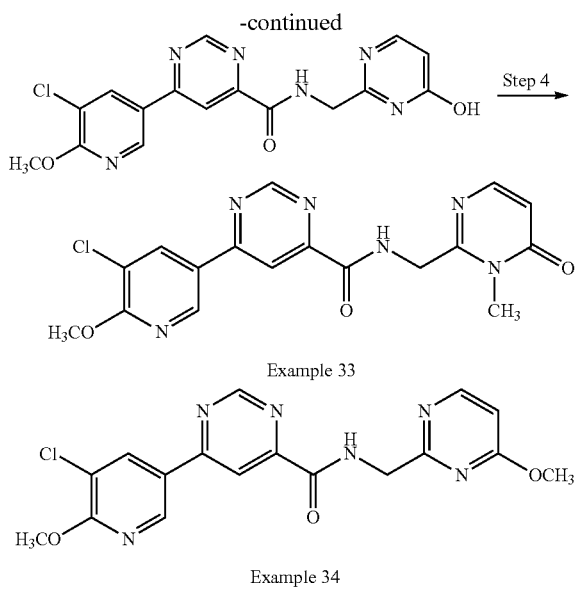

Example 33

Example 34

Examples 33 and 34: 6-(5-Chloro-6-methoxypyridin-3-yl)-N-((1-methyl-6-oxo-1,6-dihydropyrimidin-2-yl)methyl)pyrimidine-4-carboxamide and 6-(5-chloro-6-methoxypyridin-3-yl)-N-((4-methoxypyrimidin-2-yl)methyl)pyrimidine-4-carboxamide Step 1: Methyl 6-(5-chloro-6-methoxypyridin-3-yl)pyrimidine-4-carboxylate A mixture of methyl 6-chloropyrimidine-4-carboxylate (100 mg, 0.579 mmol), (5-chloro-6-methoxypyridin-3-yl)boronic acid (217 mg, 1.16 mmol), dichloro[1,1'-bis(diphenylphosphino)ferrocene]palladium dichloromethane adduct (42 mg, 0.058 mmol) and potassium phosphate (369 mg, 1.74 mmol) in DMF (5 mL) was purged with argon and heated in a sealed tube at 60° C. for 3 h. After this time, the reaction mixture was concentrated under reduced pressure, and the residue obtained was purified by FCC (Silica, 40-80% EtOAc in DCM) to give the title compound. $^1$H NMR (300 MHz, DMSO-$d_6$) δ 9.40 (d, J=1.5 Hz, 1H), 9.09 (d, J=2.1 Hz, 1H), 8.77 (d, J=2.1 Hz, 1H), 8.64 (d, J=1.2 Hz, 1H), 4.05 (s, 3H), 3.96 (s, 3H).

Step 2: 6-(5-Chloro-6-methoxypyridin-3-yl)pyrimidine-4-carboxylic acid

Lithium hydroxide (17 mg, 0.42 mmol) was added to a solution of methyl 6-(5-chloro-6-methoxypyridin-3-yl)pyrimidine-4-carboxylate (116 mg, 0.415 mmol) in THF (2.8 mL) and water (2.8 mL), and the mixture was stirred at room temperature for 3 h. After this time, the solvent was removed under reduced pressure, and water was added. The mixture was acidified to pH 2 with 2 N HCl, and the precipitate was filtered, washed with water, and dried under reduced pressure to give the title compound. $^1$H NMR (300 MHz, DMSO-$d_6$) δ 14.02 (br s, 1H), 9.39 (d, J=1.5 Hz, 1H), 9.08 (d, J=2.1 Hz, 1H), 8.75 (d, J=2.1 Hz, 1H), 8.60 (d, J=1.5 Hz, 1H), 4.05 (s, 3H).

Step 3: 6-(5-Chloro-6-methoxypyridin-3-yl)-N-((4-hydroxypyrimidin-2-yl)methyl)pyrimidine-4-carboxamide A solution of 6-(5-chloro-6-methoxypyridin-3-yl)pyrimidine-4-carboxylic acid (60 mg, 0.23 mmol), 2-(aminomethyl)pyrimidin-4-ol (31.1 mg, 0.248 mmol), HATU (112 mg, 0.294 mmol), and DIPEA (0.118 mL, 0.678 mmol) in DMF (3 mL) was stirred at rt for 16 h. After this time, the solvents were removed under reduced pressure, and the residue obtained was triturated in water (15 mL) to give the title compound. $^1$H NMR (500 MHz, DMSO-$d_6$) δ 12.61 (br s, 1H), 9.42-9.38 (m, 2H), 9.09 (d, J=3.5 Hz, 1H), 8.76 (d, J=3.5 Hz, 1H), 8.61 (d, J=2.5 Hz, 1H), 7.87 (d, J=11.0 Hz, 1H), 6.23 (d, J=11.5 Hz, 1H), 4.45 (d, J=10.0 Hz, 2H), 4.05 (s, 3H).

Step 4: 6-(5-Chloro-6-methoxypyridin-3-yl)-N-((1-methyl-6-oxo-1,6-dihydropyrimidin-2-yl)methyl)pyrimidine-4-carboxamide and 6-(5-chloro-6-methoxypyridin-3-yl)-N-((4-methoxypyrimidin-2-yl)methyl)pyrimidine-4-carboxamide A solution of 6-(5-chloro-6-methoxypyridin-3-yl)-N-((4-hydroxypyrimidin-2-yl)methyl)-pyrimidine-4-carboxamide (144 mg, 0.386 mmol), potassium carbonate (587 mg, 0.425 mmol), and methyl iodide (0.060 mL, 0.97 mmol) in DMF (3 mL) was stirred at rt for 4 h. After this time, the solvent was removed under reduced pressure, and the residue obtained was purified by FCC (Silica, 0-15% EtOAc in DCM) to give 6-(5-chloro-6-methoxypyridin-3-yl)-N-((1-methyl-6-oxo-1,6-dihydropyrimidin-2-yl)methyl)pyrimidine-4-carboxamide. $^1$H NMR (500 MHz, DMSO-$d_6$) δ 9.41 (d, J=1.0 Hz, 1H), 9.38 (t, J=5.0 Hz, 1H), 9.10 (d, J=2.0 Hz, 1H), 8.77 (d, J=2.5 Hz, 1H), 8.63 (d, J=1.5 Hz, 1H), 7.92 (d, J=6.5 Hz, 1H), 6.39 (d, J=6.5 Hz, 1H), 4.70 (d, J=5.0 Hz, 2H), 4.06 (s, 3H), 3.50 (s, 3H). Tr (UHPLC method 7)=5.23 min. m/z (ES$^+$) (M+H)$^+$ 387.0. And 6-(5-chloro-6-methoxypyridin-3-yl)-N-((4-methoxypyrimidin-2-yl)methyl)pyrimidine-4-carboxamide. $^1$H NMR (500 MHz, DMSO-$d_6$) δ 9.44 (t, J=5.5 Hz, 1H), 9.40 (d, J=1.0 Hz, 1H), 9.08 (d, J=2.0 Hz, 1H), 8.75 (d, J=2.0 Hz, 1H), 8.61 (d, J=1.0 Hz, 1H), 8.49 (d, J=6.0 Hz, 1H), 6.84 (d, J=6.0 Hz, 1H), 4.66 (d, J=6.0 Hz, 2H), 4.06 (s, 3H), 3.90 (s, 3H). Tr (UHPLC method 7)=5.60 min. m/z (ES$^+$) (M+H)$^+$ 387.1.

Method 6

Scheme for Method 6

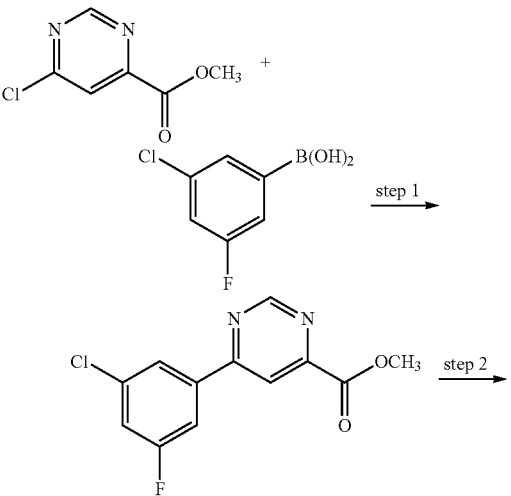

Scheme for Method 6

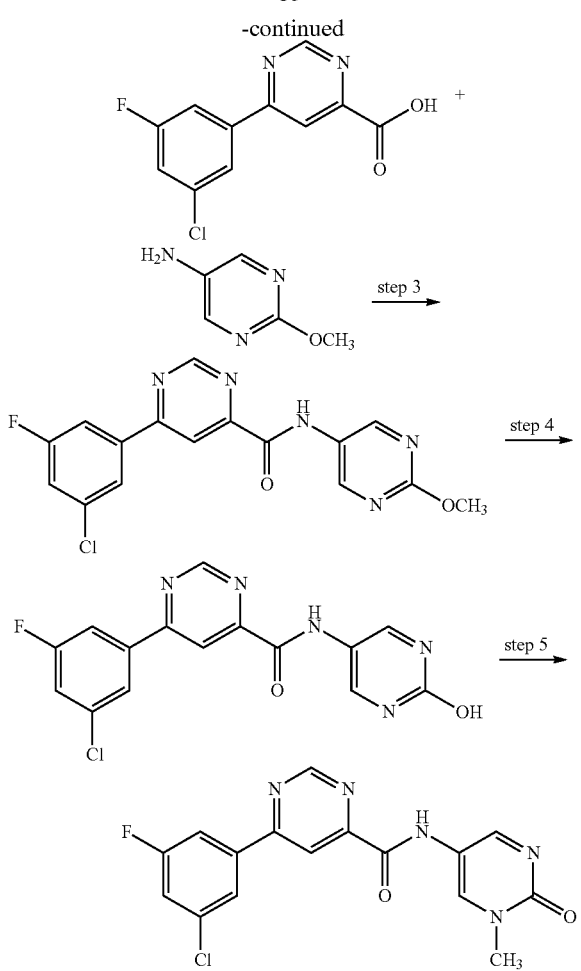

Example 35

Example 35: 6-(3-Chloro-5-fluorophenyl)-N-(1-methyl-2-oxo-1,2-dihydropyrimidin-5-yl)pyrimidine-4-carboxamide

Step 1: Methyl 6-(3-chloro-5-fluorophenyl)pyrimidine-4-carboxylate

A mixture of methyl 6-chloropyrimidine-4-carboxylate (250 mg, 1.45 mmol), (3-chloro-5-fluorophenyl)boronic acid (505 mg, 2.90 mmol), dichloro[1,1'-bis(diphenylphosphino)ferrocene]-palladium dichloromethane adduct (106 mg, 0.145 mmol) and potassium phosphate (923 mg, 4.35 mmol) in DMF (12.5 mL) was purged with argon and heated in a sealed tube at 60° C. for 3 h. After this time, the reaction mixture was concentrated under reduced pressure, and the residue obtained was purified by FCC (Silica, 0-5% MeOH in DCM). The product was rechromatographed (Silica, 40-50% ethyl acetate in hexanes) to give the title compound. $^1$H NMR (300 MHz, DMSO-$d_6$) δ 9.47 (d, J=1.2 Hz, 1H), 8.68 (d, J=1.2 Hz, 1H), 8.26 (s, 1H), 8.17 (d, J=9.9 Hz, 1H), 7.73 (d, J=8.4 Hz, 1H), 3.97 (s, 3H).

Step 2: 6-(3-Chloro-5-fluorophenyl)pyrimidine-4-carboxylic acid

Lithium hydroxide monohydrate (32 mg, 0.77 mmol) was added to a solution of methyl 6-(3-chloro-5-fluorophenyl) pyrimidine-4-carboxylate (206 mg, 0.773 mmol) in THF (5 mL) and water (5 mL), and the mixture was stirred at room temperature for 2 h. After this time, the solvent was removed under reduced pressure, and water was added. The mixture was acidified to pH 2 with 2 N HCl. The precipitate was collected by filtration, washed with water, and dried under reduced pressure to give the title compound. $^1$H NMR (300 MHz, DMSO-$d_6$) δ 14.06 (br s, 1H), 9.44 (s, 1H), 9.63 (s, 1H), 8.24 (s, 1H), 8.15 (d, J=9.3 Hz, 1H), 7.71 (d, J=8.4 Hz, 1H).

Step 3: 6-(3-Chloro-5-fluorophenyl)-N-(2-methoxypyrimidin-5-yl)pyrimidine-4-carboxamide HATU (60 mg, 0.16 mmol) was added to a mixture of 6-(3-chloro-5-fluorophenyl)-pyrimidine-4-carboxylic acid (20 mg, 0.079 mmol), 2-methoxypyrimidin-5-amine (10 mg, 0.079 mmol), and DIPEA (0.04 mL, 0.2 mmol) in DMF (2 mL), and the mixture was stirred at room temperature for 16 h. After this time, water (20 mL) was added, and the resulting precipitate was isolated by filtration and recrystallized from dimethyl sulfoxide to give the title compound. $^1$H NMR (300 MHz, DMSO-$d_6$) δ 11.30 (s, 1H), 9.53 (d, J=1.2 Hz, 1H), 9.08 (s, 2H), 8.77 (d, J=1.2 Hz, 1H), 8.29 (s, 1H), 8.20 (dt, J=9.6, 2.1 Hz, 1H), 7.74 (dt, J=8.7, 2.1 Hz, 1H), 3.93 (s, 3H).

Step 4: 6-(3-Chloro-5-fluorophenyl)-N-(2-hydroxypyrimidin-5-yl)pyrimidine-4-carboxamide Boron tribromide (1.0 M in DCM, 8.3 mL, 8.3 mmol) was added dropwise to a solution of 6-(3-chloro-5-fluorophenyl)-N-(2-methoxypyrimidin-5-yl)pyrimidine-4-carboxamide (212 mg, 0.590 mmol) in 1,2-dichloroethane (11 mL), and the mixture was heated at reflux for 48 h. After this time, water was added, and the pH was adjusted to 5 by addition of saturated sodium bicarbonate. The resulting suspension was aged for 3 h, and the solid was collected by filtration to give the title compound. $^1$H NMR (300 MHz, DMSO-$d_6$) δ 11.06 (s, 1H), 9.51 (d, J=1.5 Hz, 1H), 8.72-8.71 (m, 3H), 8.28 (s, 1H), 8.19 (dd, J=9.9, 2.1 Hz, 1H), 7.74 (dt, J=8.7, 2.1 Hz, 1H).

Step 5: 6-(3-Chloro-5-fluorophenyl)-N-(1-methyl-2-oxo-1,2-dihydropyrimidin-5-yl)pyrimidine-4-carboxamide Iodomethane (0.06 mL, 0.9 mmol) was added to a solution of 6-(3-chloro-5-fluorophenyl)-N-(2-hydroxypyrimidin-5-yl)pyrimidine-4-carboxamide (121 mg, 0.350 mmol) and potassium carbonate (53 mg, 0.39 mmol) in DMF (3.5 mL), and the mixture was stirred at rt for 2 h. After this time, the volatiles were removed under reduced pressure, and the residue obtained was purified by FCC (Silica, 0-10% MeOH in DCM) to give the title compound. $^1$H NMR (300 MHz, DMSO-$d_6$) δ 11.02 (s, 1H), 9.51 (d, J=1.2 Hz, 1H), 8.88 (d, J=3.3 Hz, 1H), 8.72-8.69 (m, 2H), 8.26 (s, 1H), 8.16 (dd, J=9.3, 2.1 Hz, 1H), 7.73 (dt, J=8.4, 2.1 Hz, 1H), 3.50 (s, 3H). Tr (UHPLC method 7)=5.08 min. m/z (ES$^+$) (M+H)$^+$ 360.0.

Method 7 Scheme for Method 7

Scheme for Method 7

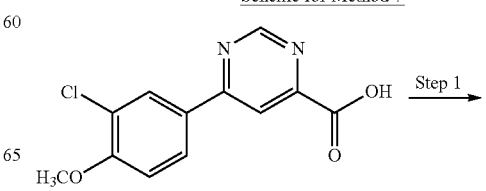

Step 1

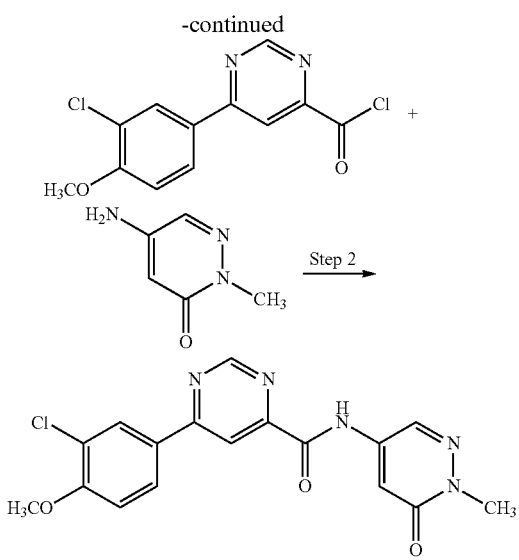

Example 36

Example 36: 6-(3-Chloro-4-methoxyphenyl)-N-(1-methyl-6-oxo-1,6-dihydropyridazin-4-yl)pyrimidine-4-carboxamide Step 1:
6-(3-Chloro-4-methoxyphenyl)pyrimidine-4-carbonyl chloride A solution of 6-(3-chloro-4-methoxyphenyl)pyrimidine-4-carboxylic acid (73 mg, 0.28 mmol) in thionyl chloride (3.82 mL, 52.4 mmol) was heated at reflux for 2 h. After this time, the volatiles were removed under reduced pressure to give the title compound. $^1$H NMR (300 MHz, CDCl$_3$) δ 9.43 (d, J=1.2 Hz, 1H), 8.29-8.27 (m, 2H), 8.10 (dd, J=8.4, 2.1 Hz, 1H), 7.08 (d, J=8.7 Hz, 1H), 4.01 (s, 3H).

Step 2: 6-(3-Chloro-4-methoxyphenyl)-N-(1-methyl-6-oxo-1,6-dihydropyridazin-4-yl)pyrimidine-4-carboxamide Sodium hydride (60% dispersion in mineral oil, 21 mg, 0.53 mmol) was added to a solution of 5-amino-2-methylpyridazin-3(2H)-one (49 mg, 0.39 mmol) in DMF (5 mL), and the mixture was stirred at rt for 30 min. 6-(3-Chloro-4-methoxyphenyl)pyrimidine-4-carbonyl chloride (100 mg, 0.353 mmol) was added, and stirring was continued for 16 h. After this time, the reaction mixture was partitioned between EtOAc and aq sat. NaHCO$_3$. The resulting precipitate was collected by filtration and lyophilized from water twice to give the title compound. $^1$H NMR (300 MHz, DMSO-d$_6$) δ 11.39 (s, 1H), 9.43 (d, J=1.2 Hz, 1H), 8.63 (d, J=1.2 Hz, 1H), 8.44-8.41 (m, 2H), 8.36 (dd, J=8.7, 2.1 Hz, 1H), 7.57 (d, J=2.4 Hz, 1H), 7.36 (d, J=9.0 Hz, 1H), 3.98 (s, 3H), 3.63 (s, 3H). Tr (UHPLC method 7)=5.33 min. m/z (ES$^+$) (M+H)$^+$ 372.1.

Also prepared by this route:

| Ex. | Structure | LCMS data |
|---|---|---|
| 37 | 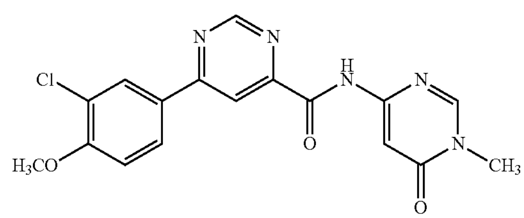 [SMILES: COc1ccc(-c2cc(C(=O)Nc3cc(=O)n(C)cn3)ncn2)cc1Cl] | Tr (UHPLC method 7) = 4.29 min, m/z (ES$^+$) (M + H)$^+$ 372.2. |
| 38 | 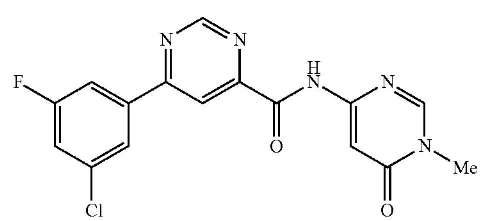 [SMILES: Cn1cnc(NC(=O)c2cc(-c3cc(F)cc(Cl)c3)ncn2)cc1=O] | Tr (UHPLC method 7) = 5.99 min, m/z (ES$^+$) (M + H)$^+$ 360.1. |
| 39 | 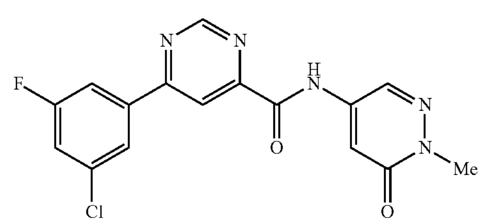 [SMILES: Cn1ncc(NC(=O)c2cc(-c3cc(F)cc(Cl)c3)ncn2)cc1=O] | Tr (UHPLC method 7) = 5.91 min, m/z (ES$^+$) (M + H)$^+$ 360.0. |

Method 8
Scheme for Method 8

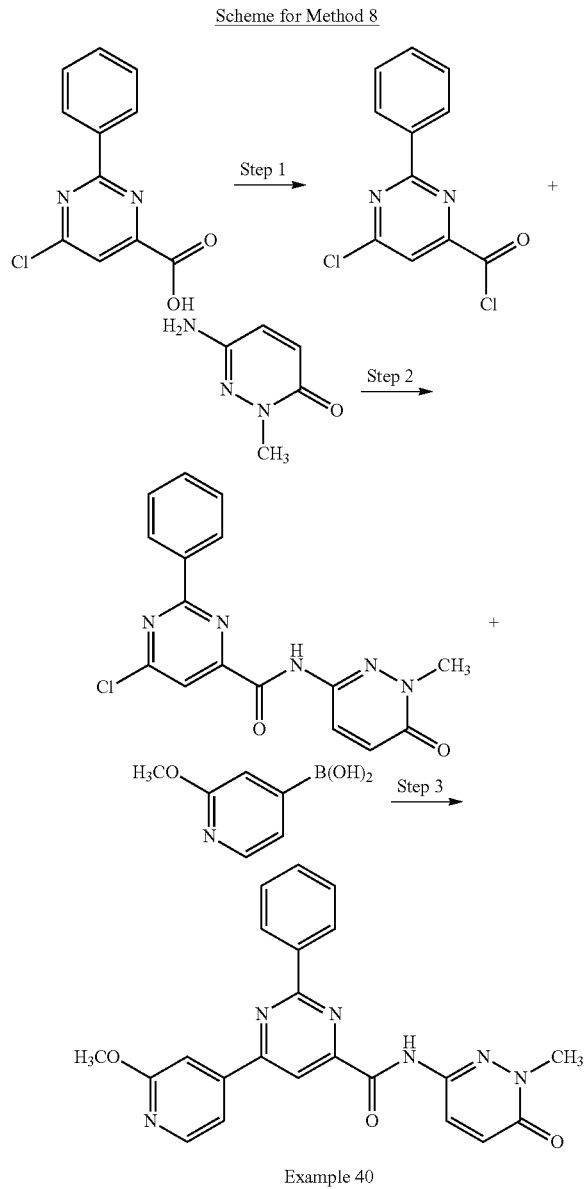

Example 40: 6-(2-Methoxypyridin-4-yl)-N-(1-methyl-6-oxo-1,6-dihydropyridazin-3-yl)-2-phenylpyrimidine-4-carboxamide Step 1: 6-Chloro-2-phenylpyrimidine-4-carbonyl chloride DMF (0.15 mL) was added to a solution of 6-chloro-2-phenylpyrimidine-4-carboxylic acid (300 mg, 1.28 mmol) in thionyl chloride (9.3 mL), and the reaction mixture was heated at reflux for 1 h. After this time, the reaction mixture was cooled to rt, diluted with toluene (30 mL) and concentrated under reduced pressure. The residue obtained was co-evaporated with toluene (10 mL) again and then dried under high vacuum for 16 h to give the title compound.

Step 2: 6-Chloro-N-(1-methyl-6-oxo-1,6-dihydropyridazin-3-yl)-2-phenylpyrimidine-4-carboxamide To a solution of 6-chloro-2-phenylpyrimidine-4-carbonyl chloride (approx. 1.28 mmol) in DCM (11 mL) was added triethylamine (0.50 mL, 3.6 mmol), 4-dimethylaminopyridine (29 g, 0.24 mmol) and 6-amino-2-methylpyridazin-3 (2H)-one (220 mg, 1.8 mmol), and the reaction mixture was stirred at rt for 16 h. After this time, water (5 mL) and EtOAc (70 mL) were added. The layers were separated, and the aqueous layer was extracted with EtOAc (2×10 mL). The combined organic layers were dried over $Na_2SO_4$, filtered and concentrated under reduced pressure. The residue obtained was adsorbed onto silica gel and purified by FCC (Silica, 0-50% EtOAc in hexanes) to give the title compound. m/z (ES$^+$) (M+H)$^+$342.1. $^1$H NMR (300 MHz, CDCl$_3$) δ 10.05 (s, 1H), 8.52-8.49 (m, 2H), 8.43 (d, J=9.9 Hz, 1H), 8.07 (s, 1H), 7.60-7.57 (m, 3H), 7.07 (d, J=9.3 Hz, 1H), 3.80 (s, 3H).

Step 3: 6-(2-Methoxypyridin-4-yl)-N-(1-methyl-6-oxo-1,6-dihydropyridazin-3-yl)-2-phenylpyrimidine-4-carboxamide A solution of (2-methoxypyridin-4-yl)boronic acid (98 mg, 0.64 mmol) in EtOH (4 mL) was added to a solution of 6-chloro-N-(1-methyl-6-oxo-1,6-dihydropyridazin-3-yl)-2-phenylpyrimidine-4-carboxamide (200 mg, 0.58 mmol) in 1,4-dioxane (8 mL). 2 M Potassium carbonate in water (0.58 mL, 1.2 mmol) and tetrakis(triphenylphosphine)palladium (0) (17 mg, 0.015 mmol) were then added, and the reaction mixture was heated at 70° C. for 2 h. After this time, the mixture was cooled to rt and concentrated under reduced pressure. The residue obtained was adsorbed onto silica gel and purified by FCC (Silica, 0-5% MeOH in DCM). The product obtained was repurified by FCC (Silica, 0-100% EtOAc in DCM), and then triturated in methylene chloride and methanol, and dried under vacuum to give the title compound. $^1$H NMR (500 MHz, DMSO-d$_6$) δ 11.25 (s, 1H), 8.82-8.80 (m, 2H), 8.57 (s, 1H), 8.43 (d, J=5.5 Hz, 1H), 8.01 (d, J=10.0 Hz, 1H), 7.96 (dd, J=5.5, 1.5 Hz, 1H), 7.79 (s, 1H), 7.63-7.62 (m, 3H), 7.11 (d, J=9.5 Hz, 1H), 3.97 (s, 3H), 3.69 (s, 3H). Tr (UHPLC method 7)=5.30 min. m/z (ES$^+$) (M+H)$^+$ 415.2.

Biological Assays

Exon1-Q46 Radioligand Binding Assay

For radioligand binding assays (RBA) MBP-HTT(1-89) Q46-His(6×) ("Exon1-Q46") protein was generated based on a previous publication (Scherzinger et al. Cell, Vol. 90, 549-558, Aug. 8, 1997). For experiments, 30 pM MBP-Exon1-Q46 was incubated with 150 µg/mL thrombin in assay buffer (150 mM NaCl, 50 mM Tris pH 8.0) and 2 mM CaCl$_2$ for 16 hours at 37° C. Aggregated Exon1-Q46 was pelleted by centrifugation for 5 minutes at 13,000 rpm in a bench top centrifuge and re-dissolved in the same volume of assay buffer. Test compounds were prepared by titration in DMSO at 11 concentrations from 63 µM to 2 nM. For the RBA, Q46 protein aggregates and test compounds were pre-incubated in assay buffer for 20 minutes at room temperature, in 100 µL/well in a 96-well plate (pp, round bottom). Then, ligand was added in 50 µL/well and incubated for 60 minutes at 37° C. Final assay concentrations were 1 µM to 30 pM test compound, 1 µM Exon1-Q46 protein (equivalent monomer concentration) and 0.3 nM ligand [$^3$H$_3$-methyl]-5-((5-methoxypyridin-2-yl)methoxy)-

2-(pyrazin-2-yl)benzo[d]oxazole. Samples were transferred onto GF/B filter plates and washed 2× with 200 μL PBS using a Filtermate Harvester. After drying filter plates for 1 hour at 55° C., the back of the plates were sealed with foil and 30 μL/well scintillation fluid (Packard MicroScint 40) added, incubated for 15 minutes in the dark and counted in a MicroBeta reader. For analysis, replicate data from independent assay plates were normalized towards 0% and 100% inhibition using control wells of vehicle (0% inhibition) and 1 μM unlabeled [$^3$H$_3$-methyl]-5-((5-methoxypyridin-2-yl)methoxy)-2-(pyrazin-2-yl)benzo[d]oxazole (100% inhibition). IC$_{50}$ values were determined with a sigmoidal inhibition model with four variables (top, bottom, slope, IC$_{50}$) in a global fit using the normalized replicate data.

The results for various example compounds were as provided in the table below (+++<100 nM; ++100-500; +500-10000; ND: not determined):

| Patent ID | Classified Potency |
| --- | --- |
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |

PET Imaging Example

The following example provides an illustrative, non-limiting, procedure that may be utilized when performing PET imaging studies on an individual in a clinical setting. The individual is either unmedicated or pre-medicated with an unlabeled compound. The individual may undergo fasting, allowing water intake ad libitum, prior to PET imaging. A 20G two-inch venous catheter is inserted into the contralateral ulnar vein for administration of the imaging agent. The human subject is positioned in the PET camera and a tracer dose of imaging agent is administered via i.v. catheter. Either arterial or venous blood samples are taken at appropriate time intervals throughout the PET scan in order to analyze and quantitate the fraction of umetabolized compound in plasma. Images are acquired for up to 120 minutes. Within ten minutes of the injection of radiotracer and at the end of the imaging session, 1 mL. blood samples are obtained for determining the plasma concentration of any unlabeled imaging agent compound (or other compound of intervention) which may have been administered before the PET tracer.

Tomographic images are obtained through image reconstruction. For example, for determining the distribution of imaging agent, regions of interest (ROIs) are drawn on the reconstructed image. Regions of interest in a brain image may include, for example, the striatum, cerebellum, or basal ganglia. Imaging agent uptake over time in these regions may be used to generate time activity curves (TAC). Data may be expressed as radioactivity per unit time per unit volume (e.g., μCi/cc/mCi injected dose), or as radioactivity per unit volume. TAC data may be processed with various methods known in the field to yield quantitative parameters, an example of which is Binding Potential (BP). For further description of imaging procedure, see, for example, Waxman A. D., et al., Society of Nuclear Medicine Procedure Guideline for FDG PET Brain Imaging, ver. 1.0, (Feb. 8, 2009).

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A compound of Formula III:

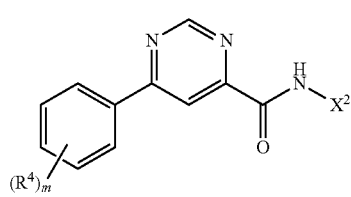

or an isotopically enriched analog, pharmaceutically acceptable salt, tautomer, stereoisomer, or a mixture of stereoisomers thereof,
wherein the compound is labeled with one or more radioactive isotopes;

$X^2$ is

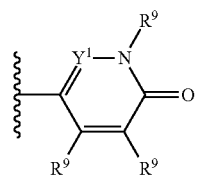

wherein $Y^1$ is N, and each $R^9$ is independently hydrogen or $R^6$;

each $R^4$ is independently halo, cyano, hydroxy, nitro, amino, alkylamino, dialkylamino, $C_{1-6}$ alkyl optionally substituted with $R^5$, $C_{1-6}$ haloalkyl, $C_{1-6}$ hydroxyalkyl, $C_{1-6}$ alkoxy optionally substituted with $R^5$, or $C_{1-6}$ haloalkoxy;

each $R^5$ is independently halo, cyano, hydroxy, amino, alkylamino, dialkylamino, or $C_{1-6}$ alkoxy;

each $R^6$ is independently halo, cyano, hydroxy, nitro, amino, alkylamino, dialkylamino, $C_{1-6}$ alkyl optionally substituted with $R^7$, $C_{1-6}$ haloalkyl, $C_{1-6}$ hydroxyalkyl, $C_{1-6}$ alkoxy optionally substituted with $R^7$, or $C_{1-6}$ haloalkoxy;

each $R^7$ is independently halo, cyano, hydroxy, amino, alkylamino, dialkylamino, or $C_{1-6}$ alkoxy; and m is 0 to 4.

2. The compound of claim 1, wherein $X^2$ is

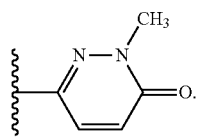

3. The compound of claim 1, wherein each $R^4$ is independently halo, cyano, $C_{1-6}$ alkyl, or $C_{1-6}$ alkoxy.

4. The compound of claim 1, wherein each $R^6$ is independently halo, $C_{1-6}$ alkyl, or $C_{1-6}$ alkoxy.

5. A compound selected from:

| Ex | Structure |
|---|---|
| 22 | ![Structure 22] |
| 23 | ![Structure 23] |
| 40 | ![Structure 40] and |
| 41 | ![Structure 41] | or an isotopically enriched analog, pharmaceutically acceptable salt, tautomer, stereoisomer, or a mixture of stereoisomers thereof, wherein the compound is labeled with one or more radioactive isotopes.

6. The compound of claim 1, wherein the compound contains one or more positron-emitting radioactive isotopes selected from $^{11}$C, $^{13}$N, $^{15}$O, and $^{18}$F.

7. An imaging agent comprising the compound of claim 6, or an isotopically enriched analog, pharmaceutically acceptable salt, tautomer, stereoisomer, or a mixture of stereoisomers thereof.

8. A method of generating diagnostic images in an individual comprising administering an effective amount of a compound of claim 1 to an individual, and generating an image of a body part or body area of the individual.

9. The method of claim 8, wherein generating an image of a body part or body area of the individual comprises generating an image to detect the presence or absence of a protein susceptible to aggregation in the image.

10. The method of claim 9, wherein the protein susceptible to aggregation is huntingtin protein (HTT protein).

11. The method of claim 9, wherein the presence or absence of a protein aggregate corresponds to the presence or absence of a neurodegenerative disease.

12. The method of claim 11, wherein the neurodegenerative disease is selected from Alzheimer's disease, amyotrophic lateral sclerosis, Huntington's disease, Parkinson's disease, Prion disease, and spinocerebellar ataxias.

13. The method of claim 12, wherein the neurodegenerative disease is Huntington's disease (HD).

14. The method of claim 8, wherein generating an image comprises positron emission tomography (PET) imaging, PET with concurrent computed tomography imaging (PET/CT), PET with concurrent magnetic resonance imaging (PET/MRI), single-photon emission computed tomography (SPECT) imaging, or a combination thereof.

* * * * *

UNITED STATES PATENT AND TRADEMARK OFFICE
CERTIFICATE OF CORRECTION

PATENT NO. : 12,036,292 B2
APPLICATION NO. : 17/395055
DATED : July 16, 2024
INVENTOR(S) : Longbin Liu et al.

It is certified that error appears in the above-identified patent and that said Letters Patent is hereby corrected as shown below:

In the Claims

In Claim 2, Column 77, Lines 30 to 37, please replace " 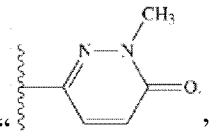 " with 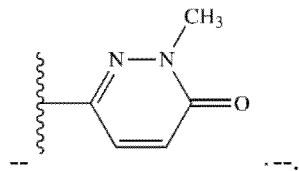 --.

Signed and Sealed this
Twenty-fourth Day of September, 2024

Katherine Kelly Vidal
*Director of the United States Patent and Trademark Office*